US012648972B2

(12) United States Patent
Lin et al.

(10) Patent No.: US 12,648,972 B2
(45) Date of Patent: Jun. 9, 2026

(54) *Lacticaseibacillus paracasei* TCI077 AND METHOD FOR CONDITIONING SKIN AND BOOSTING IMMUNITY WITH *Lacticaseibacillus paracasei* TCI077 OR METABOLITES THEREOF

(71) Applicant: TCI CO., LTD., Taipei (TW)

(72) Inventors: Yung-Hsiang Lin, Taipei (TW); Chu-Han Huang, Taipei (TW)

(73) Assignee: TCI CO., LTD., Taipei (TW)

( * ) Notice: Subject to any disclaimer, the term of this patent is extended or adjusted under 35 U.S.C. 154(b) by 220 days.

(21) Appl. No.: 18/413,001

(22) Filed: Jan. 15, 2024

(65) Prior Publication Data

US 2024/0245734 A1 Jul. 25, 2024

Related U.S. Application Data

(60) Provisional application No. 63/480,512, filed on Jan. 19, 2023.

(30) Foreign Application Priority Data

Dec. 14, 2023 (TW) ................................. 112148878

(51) Int. Cl.
| | |
|---|---|
| *A61K 35/744* | (2015.01) |
| *A61K 8/99* | (2017.01) |
| *A61P 17/10* | (2006.01) |
| *A61Q 19/00* | (2006.01) |
| *A61Q 19/08* | (2006.01) |
| *C12N 1/205* | (2026.01) |
| *C12R 1/01* | (2006.01) |

(52) U.S. Cl.
CPC .............. *A61K 35/744* (2013.01); *A61K 8/99* (2013.01); *A61P 17/10* (2018.01); *A61Q 19/00*
(2013.01); *A61Q 19/007* (2013.01); *A61Q 19/08* (2013.01); *C12N 1/205* (2021.05); *C12R 2001/01* (2021.05)

(58) Field of Classification Search
CPC ...... A61K 35/744; A61K 35/747; A61P 17/10
See application file for complete search history.

(56) References Cited

FOREIGN PATENT DOCUMENTS

| | | |
|---|---|---|
| CN | 112877260 A | 6/2021 |
| CN | 114561331 A | 5/2022 |
| CN | 114645002 A | 6/2022 |

OTHER PUBLICATIONS

McBain et al., Biomedical Sciences; Chapter: Skin Microbiology, 2016 (abstract) (Year: 2016).*
Medical News Today, 2024; https://www.medicalnewstoday.com/articles/324784#summary (Year: 2024).*

* cited by examiner

*Primary Examiner* — Brian Gangle
*Assistant Examiner* — Lakia J Jackson-Tongue
(74) *Attorney, Agent, or Firm* — Chieh-Mei Wang

(57) ABSTRACT

Provided is a composition in a form of powder, granule, solution, gel, or capsule and including an effective amount of *Lacticaseibacillus Paracasei* TC1077 deposited under an accession number of DSM 34374 for inhibiting acne, inhibiting bacteria, inhibiting inflammation, strengthening skin structure, improving skin moisture, reducing skin wrinkles, relieving skin dryness, itchiness, and redness, boosting immunity, or promoting defecation. Also provided is a method for inhibiting acne, inhibiting bacteria, inhibiting inflammation, strengthening skin structure, improving skin moisture, reducing skin wrinkles, relieving skin dryness, itchiness, and redness, boosting immunity, or promoting defecation by using the *Lacticaseibacillus Paracasei* TC1077 or metabolites thereof.

12 Claims, 9 Drawing Sheets

Specification includes a Sequence Listing.

1

*Lacticaseibacillus paracasei* TCI077 AND METHOD FOR CONDITIONING SKIN AND BOOSTING IMMUNITY WITH *Lacticaseibacillus paracasei* TCI077 OR METABOLITES THEREOF

CROSS-REFERENCES TO RELATED APPLICATIONS

This application claims the benefit of U.S. provisional application Ser. No. 63/480,512, filed on Jan. 19, 2023, and claims the priority of patent application Ser. No. 11/214, 8878, filed in Taiwan, R.O.C. on Dec. 14, 2023. The entirety of the above-mentioned patent applications are hereby incorporated by references herein and made a part of the specification.

REFERENCE OF AN ELECTRONIC SEQUENCE LISTING

The contents of the electronic sequence listing (P234135USI.xml; Size: 18,997 bytes; and Date of Creation: Jan. 12, 2024) is herein incorporated by reference in its entirety.

BACKGROUND

Technical Field

The present invention relates to *Lacticaseibacillus Paracasei*, and in particular, to *Lacticaseibacillus Paracasei* TCI077 and methods for conditioning skin and boosting immunity by using *Lacticaseibacillus Paracasei* TCI077 or metabolites thereof.

Related Art

People of all ages may have acne according to the literature. More than 60% of adolescents have social problems affected by acne (pimples). In addition, about 7% of men and 15% of women over age 50 still suffer from acne.

In order to resolve the foregoing problems, there is an urgent need for a person skilled in the aft to develop a scientifically-based and highly-effective probiotic product for the benefit of the general population in need thereof.

SUMMARY

In some embodiments. *Lacticaseibacillus Paracasei* is *Lacticaseibacillus Paracasei* TCI077 deposited under an accession number of DSM 34374.

In some embodiments, a composition for inhibiting acne, inhibiting bacteria, inhibiting inflammation, strengthening skin structure, improving skin moisture, reducing skin wrinkles, relieving skin dryness, itchiness, and redness, boosting immunity, or promoting defecation, including an effective amount of *Lacticaseibacillus Paracase*. The *Lacticaseibacillus Paracasei* is *Lacticaseibacillus Paracasei* TCI077 deposited under an accession number of DSM 34374. The composition is in a form of powder, granule, solution, gel, or capsule.

In some embodiments, a use of *Lacticaseibacillus Paracasei* or metabolites thereof for preparing a composition for inhibiting acne. The *Lacticaseibacillus Paracasei* is *Lacticaseibacillus Paracasei* TCI077 deposited under an accession number of DSM 34374.

2

In some embodiments, an anti-acne method for inhibiting acne includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, die *Lacticaseibacillus Paracasei* or the metabolites thereof inhibits and/or reduces *Propionibacterium acnes*.

In some embodiments, the *Lacticaseibacillus Paracasei* or the metabolites thereof promotes cytothesis to eliminate acne scars.

In some embodiments, the *Lacticaseibacillus Paracasei* or the metabolites thereof promotes proliferation of skin cells or keratinocytes to promote cytothesis.

In some embodiments, the *Lacticaseibacillus Paracasei* or the metabolites thereof reduces skin oil content.

In some embodiments, the *Lacticaseibacillus Paracasei* or the metabolite thereof improves skin oil-water balance.

In some embodiments, a use of *Lacticaseibacillus Paracasei* or metabolites thereof for preparing a composition for inhibiting bacteria. The *Lacticaseibacillus Paracasei* is *Lacticaseibacillus Paracasei* TCI077 deposited under an accession number of DSM 34374.

In some embodiments, a method for inhibiting bacteria includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, a use of *Lacticaseibacillus Paracasei* or metabolites thereof for preparing a composition for inhibiting inflammation. The *Lacticaseibacillus Paracasei* is *Lacticaseibacillus Paracasei* TCI077 deposited under an accession number of DSM 34374.

In some embodiments, a method for inhibiting inflammation includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, the *Lacticaseibacillus Paracasei* or the metabolites thereof inhibits inflammation of keratinocytes.

In some embodiments, a use of *Lacticaseibacillus Paracasei* or metabolites thereof for preparing a composition for strengthening skin structure. The *Lacticaseibacillus Paracasei* is *Lacticaseibacillus Paracasei* TCI077 deposited under an accession number of DSM 34374.

In some embodiments, a method for strengthening skin structure includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, the *Lacticaseibacillus Paracasei* or the metabolites thereof increases keratins.

In some embodiments, a use of *Lacticaseibacillus Paracasei* or metabolites thereof for preparing a composition for improving skin moisture. The *Lacticaseibacillus Paracasei* is *Lacticaseibacillus Paracasei* TCI077 deposited under an accession number of DSM 34374.

In some embodiments, a method for improving skin moisture includes administering to a subject in need thereof a composition including *Lacticaseibacillus Paracasei* or metabolites thereof. The *Lacticaseibacillus Paracasei* is

*Lacticaseibacillus Paracasei* TCI077 deposited under an accession number of DSM 34374.

In some embodiments, the *Lacticaseibacillus Paracasei* or the metabolites thereof increases hyaluronic acid, ceramides, natural moisturizing factors (NMFs), and/or aquaporins.

In some embodiments, a use of *Lacticaseibacillus Paracasei* or metabolites thereof for preparing a composition for reducing skin wrinkles. The *Lacticaseibacillus Paracasei* is *Lacticaseibacillus Paracasei* TCI077 deposited under an accession number of DSM 34374.

In some embodiments, a method for reducing skin wrinkles includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, a use of *Lacticaseibacillus Paracasei* or metabolites thereof for preparing a composition for relieving skin dryness, itchiness, and redness. The *Lacticaseibacillus Paracasei* is *Lacticaseibacillus Paracasei* TCI077 deposited under an accession number of DSM 34374.

In some embodiments, a method for relieving skin dryness, itchiness, and redness includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, a use of *Lacticaseibacillus Paracasei* or metabolites thereof for preparing a composition for boosting immunity. The *Lacticaseibacillus Paracasei* is *Lacticaseibacillus Paracasei* TCI077 deposited under an accession number of DSM 34374.

In some embodiments, a method for boosting immunity includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

In some embodiments, the *Lacticaseibacillus Paracasei* or the metabolites thereof increases neutrophil counts.

In some embodiments, a use of *Lacticaseibacillus Paracasei* or metabolites thereof for preparing a composition for promoting defecation. The *Lacticaseibacillus Paracasei* is *Lacticaseibacillus Paracasei* TCI077 deposited under an accession number of DSM 34374.

In some embodiments, a method for promoting defecation includes administering to a subject in need thereof a composition including *Lacticaseibacillus Paracasei* or metabolites thereof. The *Lacticaseibacillus Paracasei* is *Lacticaseibacillus Paracasei* TCI077 deposited under an accession number of DSM 34374.

Based on the above, the *Lacticaseibacillus Paracasei* or the metabolites thereof in any embodiment of the present disclosure has the effect of conditioning skin or boosting immunity. In some embodiments, the *Lacticaseibacillus Paracasei* or the metabolites thereof is suitable for preparing a composition for conditioning skin or boosting immunity. In some embodiments, a method for conditioning skin or boosting immunity includes administering to a subject in need thereof a composition including the *Lacticaseibacillus Paracasei* or the metabolites thereof. In other words, the composition has a function of conditioning skin or boosting immunity. That is to say, the composition administered to an individual can produce the effect of conditioning skin or boosting immunity on the individual. In some embodiments, the *Lacticaseibacillus Paracasei*, the metabolites thereof, or the composition prepared therefrom further has one or more of the following functions: inhibiting acne, inhibiting bacteria, inhibiting inflammation, strengthening skin structure, improving skin moisture, reducing skin wrinkles, relieving skin dryness, itchiness, and redness, boosting immunity, or promoting defecation. In some embodiments, a method for inhibiting acne, inhibiting bacteria, inhibiting inflammation, strengthening skin structure, improving skin moisture, reducing skin wrinkles, relieving skin dryness, itchiness, and redness, boosting immunity, and promoting defecation includes administering to a subject in need thereof a composition including the *Lacticaseibacillus Paracasei* or the metabolites thereof.

DETAILED DESCRIPTION

Figure 1:
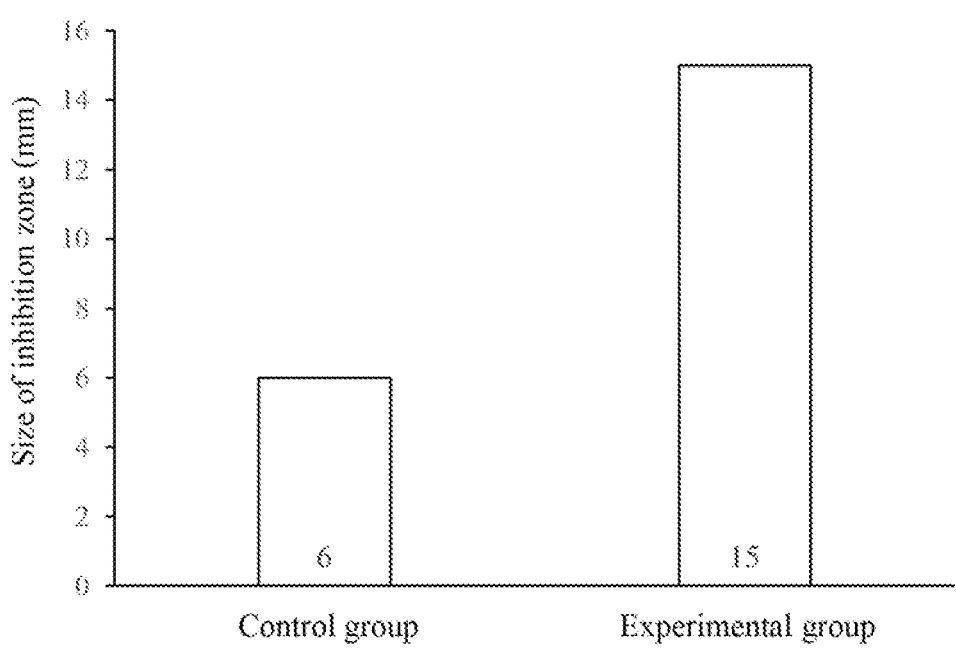
FIG. 1 is a bar chart showing the size of the inhibition zone after treated by a *Lacticaseibacillus Paracasei* TCI077 sample in accordance with some embodiments of the present disclosure.

In some embodiments. *Lacticaseibacillus Paracasei* is *Lacticaseibacillus Paracasei* TCI077. *Lacticaseibacillus Paracasei* TCI077 is deposited at Food Industry Research and Development Institute (331 Shih-Pin Road, Hsinchu 300, Taiwan) under an accession number of BCRC 911142 on Aug. 8, 2022, deposited at China General Microbiological Culture Collection Center (CGMCC, Institute of Microbiology Chinese Academy of Sciences, NO. 1 West Beichen Road, Chaoyang District, Beijing 100101, China) under an accession number of CGMCC 7.532 on March, 2023, and deposited at Leibniz Institute DSMZ-German Collection of Microorganisms and Cell Cultures GmbH (DSMZ, Inhoffenstraße 7B 38124 Braunschweig Science Campus Braunschweig-Süd, Germany) under an accession number of DSM 34374 on Sep. 7, 2022.

In some embodiments, *Lacticaseibacillus Paracasei* TCI077 is isolated from a fruiting body of *Taiwanofungus camphoratus*.

In some embodiments, the *Lacticaseibacillus Paracasei* or metabolites thereof has an anti-acne capability. Therefore, the *Lacticaseibacillus Paracasei* or the metabolites thereof is suitable for preparing an anti-acne composition.

In some embodiments, an anti-acne method includes administering to a subject in need thereof a composition including the *Lacticaseibacillus Paracasei* or the metabolites thereof.

In some embodiments, the *Lacticaseibacillus Paracasei* or the metabolites thereof has a capability of inhibiting and/or reducing *Propionibacterium acnes*. In other words, the *Lacticaseibacillus Paracasei* or the metabolites thereof administered to an individual can inhibit and/or reduce *Propionibacterium acnes* in the individual. Therefore, the *Lacticaseibacillus Paracasei* or the metabolites thereof is suitable for preparing a composition for inhibiting and/or reducing *Propionibacterium acnes*.

In some embodiments, the *Lacticaseibacillus Paracasei* or the metabolites thereof has a capability of promoting cytothesis to eliminate acne scars. In other words, the *Lacticaseibacillus Paracasei* or the metabolites thereof administered to an individual can promote cytothesis of the individual to eliminate acne scars of the individual. Therefore, the *Lacticaseibacillus Paracasei* or the metabolites thereof is suitable for preparing a composition for promoting cytothesis to eliminate acne scars.

In some embodiments, the *Lacticaseibacillus Paracasei* or the metabolites thereof has a capability of promoting proliferation of skin cells or keratinocytes to promote cytothesis. In other words, the *Lacticaseibacillus Paracasei* or the metabolites thereof administered to an individual can promote proliferation of skin cells or keratinocytes of the individual to promote cytothesis of the individual. Therefore, the *Lacticaseibacillus Paracasei* or the metabolites thereof is suitable for preparing a composition for promoting proliferation of skin cells or keratinocytes to promote cytothesis.

In some embodiments, the *Lacticaseibacillus Paracasei* or the metabolites thereof has a capability of reducing skin oil content. In other words, the *Lacticaseibacillus Paracasei* or the metabolites thereof administered to an individual can reduce skin oil content of the individual. Therefore, the *Lacticaseibacillus Paracasei* or the metabolites thereof is suitable for preparing a composition for reducing skin oil content.

In some embodiments, the *Lacticaseibacillus Paracasei* or the metabolites thereof has a capability of improving skin oil-water balance. In other words, the *Lacticaseibacillus Paracasei* or the metabolites thereof administered to an individual can improve skin oil-water balance of the individual. Therefore, the *Lacticaseibacillus Paracasei* or the metabolites thereof is suitable for preparing a composition for improving skin oil-water balance.

In some embodiments, a method for inhibiting and/or reducing *Propionibacterium acnes*, promoting cytothesis to eliminate acne scars, promoting proliferation of skin cells or keratinocytes to promote cytothesis, reducing skin oil content, improving skin oil-water balance, or any combination thereof includes administering to a subject in need thereof a composition including the *Lacticaseibacillus Paracasei* or the metabolites thereof.

In some embodiments, the *Lacticaseibacillus Paracasei* or the metabolites thereof has an antibacterial capability. Therefore, the *Lacticaseibacillus Paracasei* or the metabolites thereof is suitable for preparing an antibacterial composition.

In some embodiments, an antibacterial method includes administering to a subject in need thereof a composition including the *Lacticaseibacillus Paracasei* or the metabolites thereof.

In some embodiments, the *Lacticaseibacillus Paracasei* or the metabolites thereof has an anti-inflammatory capability. Therefore, the *Lacticaseibacillus Paracasei* or the metabolites thereof is suitable for preparing an anti-inflammatory composition.

In some embodiments, an anti-inflammatory method includes administering to a subject in need thereof a composition including the *Lacticaseibacillus Paracasei* or the metabolites thereof.

In some embodiments, the *Lacticaseibacillus Paracasei* or the metabolites thereof has a capability of inhibiting inflammation of keratinocytes. In other words, the *Lacticaseibacillus Paracasei* or the metabolites thereof administered to an individual can inhibit inflammation of keratinocytes of the individual. Therefore, the *Lacticaseibacillus Paracasei* or the metabolites thereof is suitable for preparing a composition for inhibiting inflammation of keratinocytes.

In some embodiments, a method for inhibiting inflammation of keratinocytes includes administering to a subject in need thereof a composition including the *Lacticaseibacillus Paracasei* or the metabolites thereof.

In some embodiments, the *Lacticaseibacillus Paracasei* or the metabolites thereof has a capability of strengthening skin structure. Therefore, the *Lacticaseibacillus Paracasei* or the metabolites thereof is suitable for preparing a composition for strengthening skin structure.

In some embodiments, a method for strengthening skin structure includes administering to a subject in need thereof a composition including the *Lacticaseibacillus Paracasei* or the metabolites thereof.

In some embodiments, the *Lacticaseibacillus Paracasei* or the metabolites thereof has a capability of increasing keratins. In other words, the *Lacticaseibacillus Paracasei* or the metabolites thereof administered to an individual can increase keratins of the individual. Therefore, the *Lacticaseibacillus Paracasei* or the metabolites thereof is suitable for preparing a composition for increasing keratins.

In some embodiments, a method for increasing keratins includes administering to a subject in need thereof a composition including the *Lacticaseibacillus Paracasei* or the metabolites thereof.

In some embodiments, the *Lacticaseibacillus Paracasei* or the metabolites thereof has a capability of improving skin moisture. Therefore, the *Lacticaseibacillus Paracasei* or the metabolites thereof is suitable for preparing a composition for improving skin moisture.

In some embodiments, a method for improving skin moisture includes administering to a subject in need thereof a composition including the *Lacticaseibacillus Paracasei* or the metabolites thereof.

In some embodiments, the *Lacticaseibacillus Paracasei* or the metabolites thereof has a capability of increasing hyaluronic acid, ceramides, natural moisturizing factors (NMFs), and/or aquaporins. In other words, the *Lacticaseibacillus Paracasei* or the metabolites thereof administered to an individual can increase hyaluronic acid, ceramides, natural moisturizing factors (NMFs), and/or aquaporins of the individual. Therefore, the *Lacticaseibacillus Paracasei* or the metabolites thereof is suitable for preparing a composition for increasing hyaluronic acid, ceramides, natural moisturizing factors (NMFs), and/or aquaporins.

In some embodiments, a method for increasing hyaluronic acid, ceramides, natural moisturizing factors (NMFs), and/or aquaporins includes administering to a subject in need thereof a composition including the *Lacticaseibacillus Paracasei* or the metabolites thereof.

In some embodiments, the *Lacticaseibacillus Paracasei* or the metabolites thereof has a capability of reducing skin wrinkles. Therefore, the *Lacticaseibacillus Paracasei* or the metabolites thereof is suitable for preparing a composition for reducing skin wrinkles.

In some embodiments, a method for reducing skin wrinkles includes administering to a subject in need thereof a composition including the *Lacticaseibacillus Paracasei* or the metabolites thereof.

In some embodiments, the *Lacticaseibacillus Paracasei* or the metabolites thereof has a capability of relieving dry, itchy, and red skin. Therefore, the *Lacticaseibacillus Paracasei* or the metabolites thereof is suitable for preparing a composition for relieving dry, itchy, and red skin.

In some embodiments, a method for relieving dry, itchy, and red skin includes administering to a subject in need thereof a composition including the *Lacticaseibacillus Paracasei* or the metabolites thereof.

In some embodiments, the *Lacticaseibacillus Paracasei* or the metabolites thereof has a capability of boosting immunity. Therefore, the *Lacticaseibacillus Paracasei* or the metabolites thereof is suitable for preparing a composition for boosting immunity.

In some embodiments, a method for boosting immunity includes administering to a subject in need thereof a composition including the *Lacticaseibacillus Paracasei* or the metabolites thereof.

In some embodiments, the *Lacticaseibacillus Paracasei* or the metabolites thereof has a capability of increasing neutrophils. In other words, the *Lacticaseibacillus Paracasei* or the metabolites thereof administered to an individual can increase neutrophils of the individual. Therefore, the *Lacticaseibacillus Paracasei* or the metabolites thereof is suitable for preparing a composition for increasing neutrophils.

In some embodiments, a method for increasing neutrophils includes administering to a subject in need thereof a composition including the *Lacticaseibacillus Paracasei* or the metabolites thereof.

In some embodiments, the *Lacticaseibacillus Paracasei* or the metabolites thereof has a capability of promoting defecation. Therefore, the *Lacticaseibacillus Paracasei* or the metabolites thereof is suitable for preparing a composition for promoting defecation.

In some embodiments, a method for promoting defecation includes administering to a subject in need thereof a composition including the *Lacticaseibacillus Paracasei* or the metabolites thereof.

In some embodiments, the *Lacticaseibacillus Paracasei* is included, in the form of bacterial powder, in the composition.

In some embodiments, the *Lacticaseibacillus Paracasei* is included, in the form of live or dead bacteria, in the composition.

In some embodiments, the *Lacticaseibacillus Paracasei* is included, in the form of bacterial particulate, in the composition. The bacterial particulate comprises the *Lacticaseibacillus Paracasei* TCI077, a first covering layer and a second covering layer. The first covering layer is in-between a cell membrane and a cell wall of the *Lacticaseibacillus Paracasei* TCI077 and the *Lacticaseibacillus Paracasei* TCI077 is dispersed in the second covering layer. The first covering layer and the second covering layer can protect the *Lacticaseibacillus Paracasei* TCI077 from damage or even death.

In some embodiments, the bacterial particulate further comprises a third covering layer, and the third covering layer is outside and covering the second covering layer. The third covering layer can also protect the *Lacticaseibacillus Paracasei* TCI077 from damage or even death.

In some embodiments, the first covering layer comprises at least one of isomalto-oligosaccharide (IMO), lactose, trehalose, galactose, fructose, glucose, maltose, sucrose, fructooligosaccharide (FOS), rhamnose and raffinose. In an embodiment of the present invention, the first covering layer comprises lactose.

In some embodiments, the second covering layer comprises at least one of maltodextrin, skim milk powder, inulin and starch. In an embodiment of the present invention, the second covering layer comprises maltodextrin.

In some embodiments, the third covering layer comprises at least one of maltodextrin, arabic gum, chocolate and skim milk powder. In some embodiments, the third covering layer comprises maltodextrin, skim milk powder or a combination thereof. In an embodiment of the present invention, the third covering layer comprises skim milk powder.

In some embodiments, the oligosaccharide is semi-permeable to bacterial cells, and the oligosaccharide can permeate into a space between the cell wall and cell membrane of the *Lacticaseibacillus Paracasei* TCI077.

In some embodiments, an effective amount of the *Lacticaseibacillus Paracasei* is 50 mg/day. In some embodiments, an effective amount of the *Lacticaseibacillus Paracasei* is 1500 CFU/day.

In some embodiments, the individual or the subject may be a human.

In some embodiments, the composition may be a pharmaceutical composition or an edible composition for non-medical purposes.

In some embodiments, when the composition is a pharmaceutical composition, the pharmaceutical composition includes an effective amount of *Lacticaseibacillus Paracasei*. The pharmaceutical composition may be prepared into a dosage form for enteral, parenteral, oral, or topical administration by using techniques well known to a person skilled in the art.

In some embodiments, the dosage form for enteral or oral administration may be, but is not limited to, a tablet, a troche, a lozenge, a pill, a capsule, dispersible powder, granules, a solution, a suspension, an emulsion, syrup, an elixir, slurry, or the like.

In some embodiments, the dosage form for parenteral or topical administration may be, but is not limited to, an injection (for example, a sterile aqueous solution or dispersion), sterile powder, an external preparation, or the like.

In some embodiments, the injection for administration may include, but is not limited to, intraperitoneal injection, subcutaneous injection, intraepidermal injection, intradermal injection, intramuscular injection, intravenous injection, or intralesional injection.

In some embodiments, the pharmaceutical composition including an effective amount of *Lacticaseibacillus Paracasei* may further include a pharmaceutically acceptable carrier widely used in drug manufacturing technologies. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The type and quantity of the carrier to be used are within the professional and routine skills of a person skilled in the art. A solvent for the pharmaceutically acceptable carrier may be water, normal saline, phosphate buffered saline (PBS), or an alcohol-containing aqueous solution.

In some embodiments, the pharmaceutical composition including an effective amount of *Lacticaseibacillus Paracasei* may be prepared into an external preparation for topical administration on skin by using techniques well known to a person skilled in the art. In some embodiments, the external preparation includes, but is not limited to, an emulsion, gel, an ointment, a cream, a patch, a liniment, powder, an aerosol, a spray, a lotion, serum, paste, foam, drops, a suspension, a salve, and a bandage.

In some embodiments, when the pharmaceutical composition is an external preparation, the pharmaceutical composition may be obtained by mixing an effective amount of *Lacticaseibacillus Paracasei* and a base well known to a person skilled in die art.

In some embodiments, the base may include one or more of the following additives: water, alcohols, glycol, hydrocarbons (such as petroleum jelly and white petrolatum), wax (such as paraffin and yellow wax), preserving agents, anti-oxidants, surfactants, absorption enhancers, stabilizing agents, gelling agents (such as Carbopol® 974P, microcrystalline cellulose, and carboxymethylcellulose), active agents, humectants, odor absorbers, fragrances, pH adjusting agents, chelating agents, emulsifiers, occlusive agents, emollients, thickeners, solubilizing agents, penetration enhancers, anti-irritants, colorants, propellants, and the like.

The selection and quantity of these additives are within the professional and routine skills of a person skilled in the art.

In some embodiments, when the composition is an edible composition, the edible composition includes an effective amount of *Lacticaseibacillus Paracasei*. The edible composition may be in the form of powder, granules, solutions, gel, or paste.

In some embodiments, the edible composition for non-medical purposes including *Lacticaseibacillus Paracasei* may be a food product or a food additive.

In some embodiments, the edible composition including *Lacticaseibacillus Paracasei* may be beverages, fermented foods, bakery products, health foods, dietary supplements, or the like. In some embodiments, the edible composition including *Lacticaseibacillus Paracasei* may further include an adjuvant. For example, the adjuvant may be maltodextrin, malic acid, sucralose, citric acid, fruit flavors, honey flavors, steviol glycoside, or a combination thereof. The type and quantity of the selected adjuvant to be used are within the professional and routine skills of a person skilled in the art.

In some embodiments, the food additive may be a seasoning, a sweetener, a flavor, a pH adjusting agent, an emulsifier, a colorant, a stabilizing agent, or the like.

The experimental steps in the following examples are carried out at room temperature (about 25° C.) and at atmospheric pressure (1 atm) unless otherwise specified.

Example 1: Strain Identification

First, an isolated strain f-om a fruiting body of *Taiwanofungus camphoratus* (purchased from Chinese Medicine Shop, No. 135, Sec. 1, Dihua Street, Datong District, Taipei City, Taiwan, origin in Taiwan) was identified. The isolated strain was subjected to polymerase chain reaction (PCR) to obtain a PCR product. The PCR product was sequenced by Sanger sequencing to obtain a 16S ribosomal gene (16S rDNA) sequence (that is, SEQ ID NO: 1). Then, the sequence of SEQ ID NO: 1 was compared with 16S ribosomal gene (16S rDNA) sequences of other *Lacticaseibacillus Paracasei* 6 as shown in Table 1) on the website of National Center for Biotechnology Information (NCBI). It can be learned that the 16S rDNA sequence of the isolated strain has 98.01% to 98.17% identity (Per. Ident) to the 16S rDNA sequences of other *Lacticaseibacillus Paracasei* (as shown in Table 1). Therefore, the isolated strain was named *Lacticaseibacillus Paracasei* TCI077.

TABLE 1

| *Lacticaseibacillus Paracasei* | Identity (Per. Ident) |
| --- | --- |
| *Lactobacillus paracasei* strain MLG1-5 16S ribosomal RNA gene, partial sequence | 98.09% |
| *Lactobacillus paracasei* strain XT8-3 16S ribosomal RNA gene, partial sequence | 98.09% |
| *Lactobacillus paracasei* strain 6522 16S ribosomal RNA gene, partial sequence | 98.17% |
| *Lactobacillus paracasei* strain 4894 16S ribosomal RNA gene, partial sequence | 98.17% |
| *Lactobacillus paracasei* strain IMAU9834I 16S ribosomal RNA gene, partial sequence | 98.01% |
| *Lactobacillus paracasei* strain 8034 16S ribosomal RNA gene, partial sequence | 98.09% |
| *Lactobacillus paracasei* strain 6378 16S ribsomal gene, partial sequence | 98.17% |

*Lacticaseibacillus paracasei* was formerly known as *Lactobacillus paracasei*.

Example 2: Preservation and Culture Experiments
of *Lacticaseibacillus Paracasei* TCI077

A. Preservation and Culture Material:

1. MRS broth, purchased from BD, product No. 288130.

B. Preservation and Culture Procedure:

1. *Lacticaseibacillus Paracasei* TCI077 isolated in Example 1 was cultured in the MRS broth to obtain a bacteria solution. The bacteria solution was then mixed with glycerol in a ratio of 4:1. Then, the mixed solution of the bacteria solution and the glycerol was preserved at −80° C.

2. The mixed solution containing *Lacticaseibacillus Paracasei* TCI077 was inoculated in the MRS broth in an amount of 5% (v/v) (about $1\times10^4$ CFU/mL), and cultured at 37±1° C. and pH 6.0±0.1 in an anaerobic environment for 12 h to form a *Lacticaseibacillus Paracasei* TCI077 bacterial solution.

3. The *Lacticaseibacillus Paracasei* TCI077 bacterial solution was centrifuged to obtain a supernatant. The supernatant was filtered with a 0.22 μm filter membrane to obtain a filtrate, which is a *Lacticaseibacillus Paracasei* TCI077 sample (in other words, the *Lacticaseibacillus Paracasei* TCI077 sample contains metabolites of *Lacticaseibacillus Paracasei* TCI077).

Example 3: Antibacterial Test

A. Material and Apparatus:

1. Agar (purchased from BD, product No. 288210).

2. $1\times10^8$ CFU/mL of *Propionibacterium acnes* solution (purchased from Bioresource Collection and Research Center (BCRC, Taiwan), product No. 10723), prepared into a 10% bacteria solution, that is, $1\times10^7$ CU/mL of bacteria solution.

3. *Lacticaseibacillus Paracasei* TCI077 sample: $1\times10^8$ CFU/mL of *Lacticaseibacillus Paracasei* TCI077 bacterial solution prepared in Example 2 was centrifuged to obtain a supernatant. The supernatant was filtered with a 0.22 μm filter membrane to obtain a filtrate, which is a *Lacticaseibacillus Paracasei* TCI077 sample (in other words, the *Lacticaseibacillus Paracasei* TCI077 sample contains metabolites of *Lacticaseibacillus Paracasei* TCI077).

4. Paper disc (purchased from ADVANTEC, product No. 49005030).

B. Test Procedure:

1. An agar plate was prepared with agar.

2. The 10% bacteria solution was uniformly inoculated on the agar plate to obtain a 10% bacteria plate. In this case, there were two 10% bacteria plates respectively used as a control group and an experimental group.

3-1. Control group: A paper disc that was not immersed in any sample was inoculated on the 10% bacteria plate of the control group.

3-2. Experimental group: A paper disc was completely immersed in 200 μL of *Lacticaseibacillus Paracasei* TCI077 sample, and then the paper disc was inoculated on the 10% bacteria plate of the experimental group.

4. The bacteria plates were cultured at 37° C. for 24 h.

5. After 24 hours of culture, a diameter (mm) of an inhibition zone was measured.

C. Test Results:

Refer to FIG. 1. A diameter of an inhibition zone in the control group was 6 mm, and a diameter of an inhibition zone in the experimental group was 15 mm. To be specific, compared with the control group, about 150% of inhibition zone was increased in the experimental group with the *Lacticaseibacillus Paracasei* TCI077 sample added.

It can be learned from the test results that the *Lacticaseibacillus Paracasei* TCI077 sample can significantly improve the effect of inhibiting *Propionibacterium acnes*. *Propionibacterium acnes* is the pathogenic bacteria that mainly cause acne. In other words, as verified by the experiment, the *Lacticaseibacillus Paracasei* TCI077 or the metabolites thereof can inhibit and/or reduce *Propionibacterium acnes*, which has the effect of conditioning skin microbiota and has the effect of anti-acne and reducing the formation of acne and/or pimples. The *Lacticaseibacillus Paracasei* TCI077 or the metabolites thereof can inhibit the growth of pathogenic bacteria, which has the antibacterial effect.

Example 4: Skin Cell Proliferation Test

A. Material and Apparatus:

1. Cell line: Human skin fibroblasts, purchased from BCRC, with a cell number of 60153, hereinafter referred to as CCD-966SK cells.

2. Cell culture medium: Minimum essential medium (Eagle) in Earle's BSS (purchased from Gibco, product No. 61100-053), with 10% fetal bovine serum (purchased from Gibco, product No. 16000-044), 1 mM sodium pyruvate (purchased from Gibco, product No. 11360-070), 2.2 g/L sodium bicarbonate ($NaHCO_3$, purchased from Sigma, product No. S5761-500G), and 0.1 mM non-essential amino acids added. The 0.1 mM non-essential amino acids were obtained by adding a MEM non-essential amino acid solution (100×, purchased from Gibco, product No. 11140050) to the MEM. The MEM was 99 times the volume of the MEM non-essential amino acid solution for dilution.

3. Cell culture medium for positive control group: Minimum essential medium (Eagle) in Earle's BSS (purchased from Gibco, product No. 61100-053), with 20% fetal bovine serum (purchased from Gibco, product No. 16000-044), 1 mM sodium pyruvate (purchased from Gibco, product No. 11360-070), 2.2 g/L sodium bicarbonate ($NaHCO_3$, purchased from Sigma, product No. S5761-500G), and 0.1 mM non-essential amino acids added. The 0.1 mM non-essential amino acids were obtained by adding a MEM non-essential amino acid solution (100×, purchased from Gibco, product No. 11140050) to the MEM. The MEM was 99 times the volume of the MEM non-essential amino acid solution for dilution.

4. Assay kit: Cell proliferation assay kit (Click-iT™ Plus EdU Flow Cytometry Assay Kits-Alexa Fluor™ 488 picolyl azide, 50 tests), purchased from Invitrogen, product No. C10632.

5. Flow cytometer, purchased from BD.

B. Test Procedure:

1. The CCD-966SK cells were inoculated into a 6-well culture plate in a density of $1\times10^5$ cells per well, and cultured at 37° C. until the cell confluency reached 80% to 90%. In this case, the CCD-966SK cells were divided into three test groups: a blank group, a positive control group, and an experimental group. The test for each group was repeated for three times.

2. The culture medium in each group was replaced with an experiment medium after the cell confluency reached 80% to 90%, and then cultured at 37° C. for 24 h. The experiment medium in the blank group was the cell culture medium without the sample. The experiment medium in the positive control group was the cell culture medium for positive control group without the sample. The experiment medium in the experimental group was the cell culture medium containing 0.25% (v/v) of the *Lacticaseibacillus Paracasei* TCI077 sample prepared in Example 2.

3. After 24 hours of culture, a DNA content of each group was measured using the cell proliferation assay kit. In this case, after the cells in each group were treated according to the test procedure provided in the cell proliferation assay kit, the excitation light parameter of the flow cytometer was set to 488 nm, and the emission light parameter of the flow cytometer was set to 530/30 nm, and then the fluorescent signal of each group was detected by using the flow cytometer.

C. Test Results:

A skin cell proliferation rate of each group was analyzed based on the DNA content of each group. The relative skin cell proliferation rate of each group was calculated according to the following formula: relative skin cell proliferation rate (%)=(fluorescent signal of each group/fluorescent signal of blank group)×100%.

Statistically significant differences between the results of the blank group and the other groups were analyzed by the student t-test. In the figure, "*" means that the p value was less than 0.05 when compared with the blank group, "" means that the p value was less than 0.01 when compared with the blank group, and "*" means that the p value was less than 0.001 when compared with the blank group.

Figure 2:
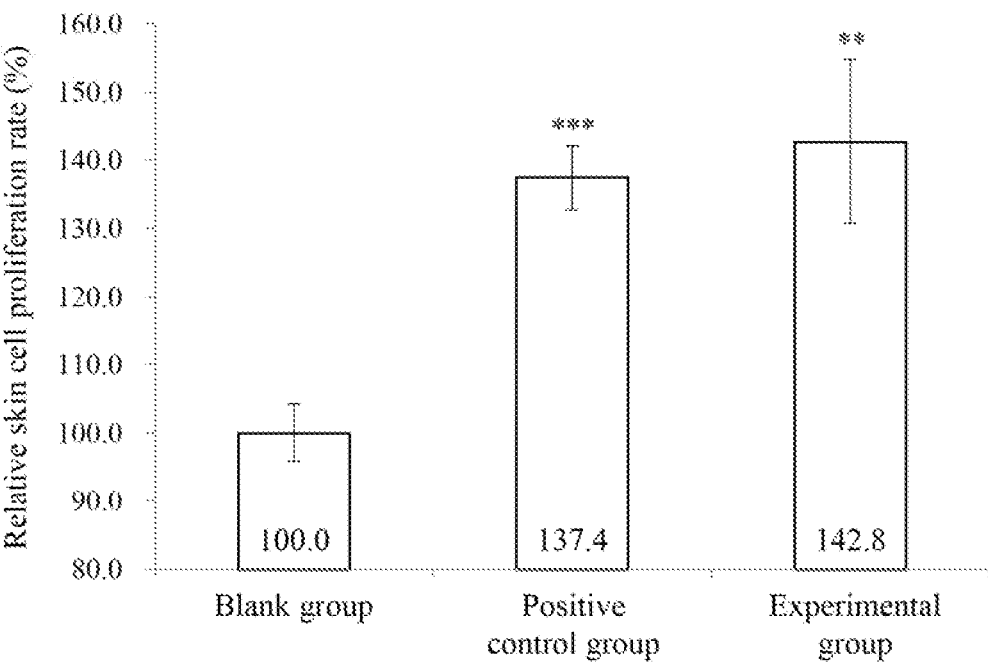
FIG. 2 is a bar chart showing the relative skin cell proliferation rate after treated by a *Lacticaseibacillus Paracasei* TCI077 sample in accordance with some embodiments of the present disclosure.

Refer to FIG. 2. The blank group was not treated with the sample, so the test results of the blank group represented the performance of the CCD-966SK cells under a normal physiological metabolism condition. In this case, when the relative skin cell proliferation rate of the blank group was set to 100%, the relative skin cell proliferation rate of the positive control group was 137.4%, and the relative skin cell proliferation rate of the experimental group was 142.8%. To be specific, compared with the blank group, the relative skin cell proliferation rate of the positive control group was significantly increased by about 37.4% after the CCD-966SK cells in the positive control group were treated with 20% fetal bovine serum. Compared with the blank group, the relative skin cell proliferation rate of the experimental group was significantly increased by about 42.8% after the CCD-%6SK cells in the experimental group were treated with the *Lacticaseibacillus Paracasei* TCI077 sample. Compared with the positive control group, the relative skin cell proliferation rate of the experimental group was increased by about 3.9% after the CCD-966SK cells in the experimental group were treated with the *Lacticaseibacillus Paracasei* TCI077 sample.

It can be learned from the test results that the *Lacticaseibacillus Paracasei* TCI077 sample can significantly promote the proliferation of skin fibroblasts. In addition, the *Lacticaseibacillus Paracasei* TCI077 sample promotes the proliferation of skin fibroblasts better than the positive control group. In other words, as verified by the experiment, the *Lacticaseibacillus Paracasei* TCI077 or the metabolites thereof can promote the proliferation of skin cells and promote the growth of skin cells, to promote skin cell repair and eliminate acne scars.

Example 5: Keratinocyte Proliferation Test

A. Material and Apparatus:

1. Cell line: Human keratinocytes, purchased from BCRC, with a cell number of T0020001, hereinafter referred to as HaCaT cells.

2. Cell culture medium: Dulbecco's modified Eagle's medium (DMEM, purchased from Gibco, product No. 12100-038), with 1% antibiotics (purchased from Invivogen, product No. ant-mpp) and 10% fetal bovine serum (purchased from Gibco, product No. 10437-028) added.

3. Cell culture medium for positive control group: Dulbecco's modified Eagle's medium (DMEM, purchased from Gibco, product No. 12100-038), with 1% antibiotics (purchased from Invivogen, product No. ant-mpp) and 20% fetal bovine serum (purchased from Gibco, product No. 10437-028) added.

4. Assay kit: Cell proliferation assay kit (Click-iT™ Plus EdU Flow Cytometry Assay Kits-Alexa Fluor™ 488 picolyl azide, 50 tests), purchased from Invitrogen, product No. C10632.

5. Flow cytometer, purchased from BD.

B. Test Procedure:

1. The HaCaT cells were inoculated into a 6-well culture plate in a density of $1\times10^5$ cells per well, and cultured at 37° C. until the cell confluency reached 80% to 90%. In this case, the HaCaT cells were divided into three test groups: a blank group, a positive control group, and an experimental group. The test for each group was repeated for three times.

2. The culture medium in each group was replaced with an experiment medium after the cell confluency reached 80% to 90%, and then cultured at 37° C. for 24 h. The experiment medium in the blank group was the cell culture medium without the sample. The experiment medium in the positive control group was the cell culture medium for positive control group without the sample. The experiment medium in the experimental group was the cell culture medium containing 0.25% (v/v) of the *Lacticaseibacillus Paracasei* TCI077 sample prepared in Example 2.

3. After 24 hours of culture, a DNA content of each group was measured using the cell proliferation assay kit. In this case, after the cells in each group were treated according to the test procedure provided in the cell proliferation assay kit, the excitation light parameter of the flow cytometer was set to 488 nm, and the emission light parameter of the flow cytometer was set to 530/30 nm, and then the fluorescent signal of each group was detected by using the flow cytometer.

C. Test Results:

A keratinocyte proliferation rate of each group was analyzed based on the DNA content of each group. The relative keratinocyte proliferation rate of each group was calculated according to the following formula: relative keratinocyte proliferation rate (%)=(fluorescent signal of each group/fluorescent signal of blank group)×100%.

Statistically significant differences between the results of the blank group and the other groups were analyzed by the student t-test. In the figure, "#" means that the p value was less than 0.05 when compared with the blank group, "##" means that the p value was less than 0.01 when compared with the blank group, and "###" means that the p value was less than 0.001 when compared with the blank group.

Figure 3:
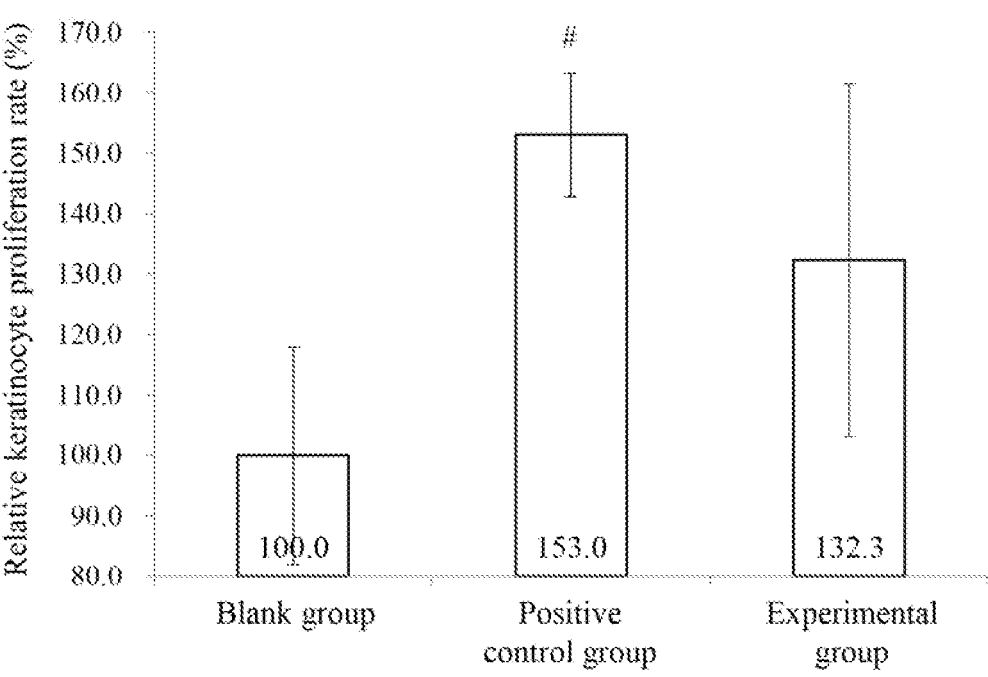
FIG. 3 is a bar chart showing the relative keratinocyte proliferation rate after treated by a *Lacticaseibacillus Paracasei* TCI077 sample in accordance with some embodiments of the present disclosure.

Refer to FIG. 3. The blank group was not treated with the sample, so the test results of the blank group represented the performance of the HaCaT cells under a normal physiological metabolism condition. In this case, when the relative keratinocyte proliferation rate of the blank group was set to 100%, the relative keratinocyte proliferation rate of the positive control group was 153.0%, and the relative keratinocyte proliferation rate of the experimental group was 132.3%. To be specific, compared with the blank group, the relative keratinocyte proliferation rate of the positive control group was significantly increased by about 53.0% after the HaCaT cells in the positive control group were treated with 20% fetal bovine serum. Compared with the blank group, the relative keratinocyte proliferation rate of the experimental group was increased by about 32.3% after the HaCaT cells in the experimental group were treated with the *Lacticaseibacillus Paracasei* TCI077 sample.

It can be learned from the test results that the *Lacticaseibacillus Paracasei* TCI077 sample can significantly promote the proliferation of keratinocytes. In other words, as verified by the experiment, the *Lacticaseibacillus Paracasei* TCI077 or the metabolites thereof can promote the proliferation of keratinocytes and promote the growth of keratinocytes, to promote keratinocyte repair and eliminate acne scars.

Example 6: IL-8 Secretion Test

A. Material and Apparatus:

1. Cell line: Human primary epidermal keratinocytes, purchased from American Type Culture Collection (ATCC), with a cell number of PCS-200-010TM, hereinafter referred to as HEKn cells.

2. Cell culture medium: Keratinocyte-specialized serum-free medium (Keratinocyte-SFM), purchased from Gibco, product No. 10724-011.

3. Lipopolysaccharide (LPS), purchased from Sigma, product No. SI-L2880-25MG.

4. Assay kit: Human CXCL8/IL8 ELISA assay kit, purchased from R&D systems, product No. D8000C.

5. Apparatus: Microplate Spectrophotometer (ELISA reader), purchased from BioTek (USA).

B. Test Procedure:

1. The keratinocytes were inoculated into a 24-well culture plate containing 500 μL of the cell culture medium per well in a density of $5 \times 10^4$ cells per well, and cultured at 37° C. for 24 h. In this case, the keratinocytes were divided into three test groups: a blank group, a control group, and an experimental group. The test for each group was repeated for three times.

2. The culture medium in each group was replaced with an experiment medium after 24 hours of culture, and then cultured at 37° C. for 24 h. The experiment medium in the blank group was the cell culture medium without LPS and the sample. The experiment medium in the control group was the cell culture medium containing 4 μg/mL of LPS. The experiment medium in the experimental group was the cell culture medium containing 4 μg/mL of LPS and 0.5% (v/v) of the *Lacticaseibacillus Paracasei* TCI077 sample prepared in Example 2.

3. 120 μL of the experiment medium was took out from each well in each group after culture for the IL-8 secretion measurement, and the level of IL-8 secreted by the keratinocytes in each group was measured using the Human CXCL8/IL8 ELISA assay kit. In this case, after the experiment medium in each group was treated according to the test procedure provided in the Human CXCL8/IL8 ELISA assay kit, the absorbance value at 450 nm ($OD_{450}$ value) of each well was measured using the ELISA reader.

C. Test Results:

The relative IL-8 secretion level of each group was calculated according to the following formula: relative IL-8 secretion level (%)=($OD_{450}$ value of each group/$OD_{450}$ value of blank group)×100%.

Statistically significant differences between the results of the blank group and the other groups and statistically significant differences between the results of the control group and the other groups were analyzed by the student t-test. In the figure, "#" means that the p value was less than 0.05 when compared with the blank group. "##" means that the p value was less than 0.01 when compared with the blank group, and "###" means that the p value was less than 0.001 when compared with the blank group. In the figure, "*" means that the p value was less than 0.05 when compared with the control group, "" means that the p value was less than 0.01 when compared with the control group, and "*" means that the p value was less than 0.001 when compared with the control group.

Figure 4:
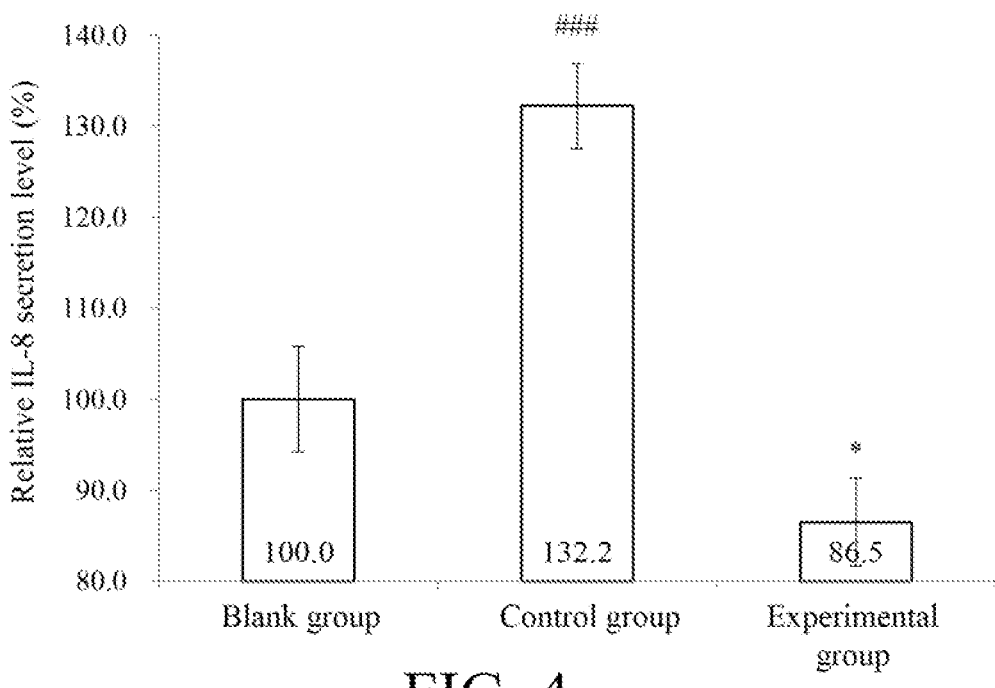
FIG. 4 is a bar chart showing the relative IL-8 secretion level after treated by a *Lacticaseibacillus Paracasei* TCI077 sample in accordance with some embodiments of the present disclosure.

Refer to FIG. 4. The blank group was not treated with the sample nor stimulated with LPS, so the test results of the blank group represented the performance of the cells under a normal physiological metabolism condition. In this case, when the relative IL-8 secretion level of the blank group was set to 100%, the relative IL-8 secretion level of the control group was 132.2%, and the relative IL-8 secretion level of the experimental group was 86.5%. To be specific, compared with the blank group, the relative IL-8 secretion level of the control group was significantly increased by about 32.2% after the cells in the control group were stimulated with LPS. Compared with the blank group, the relative IL-8 secretion level of the experimental group was reduced by about 13.5% after the cells in the experimental group were treated with the *Lacticaseibacillus Paracasei* TCI077 sample and stimulated with LPS. Compared with the control group, the relative IL-8 secretion level of the experimental group was significantly reduced by about 34.6% after the cells in the experimental group were treated with the *Lacticaseibacillus Paracasei* TCI077 sample and stimulated with LPS.

LPS is an endotoxin that can elicit a strong immune response, including an inflammatory response. Interleukin-8 (IL-8) is a cytokine secreted by macrophages and epithelial cells, and is involved in the inflammatory response.

It can be learned from the test results that the *Lacticaseibacillus Paracasei* TCI077 sample can significantly reduce the IL-8 secretion level that was increased after the keratinocytes were stimulated with LPS, to a level far below that produced by the keratinocytes under a normal physiological metabolism condition. In other words, as verified by the experiment, the *Lacticaseibacillus Paracasei* TCI077 or the metabolites thereof can inhibit and/or reduce the secretion of IL-8 by keratinocytes, and inhibit and/or reduce the level of IL-8 in keratinocytes, to reduce and/or inhibit the inflammatory state of keratinocytes. The *Lacticaseibacillus Paracasei* TCI077 or the metabolites thereof can reduce and/or inhibit the production of inflammatory substances in skin, and inhibit skin inflammation. The *Lacticaseibacillus Paracasei* TCI077 or the metabolites thereof can reduce and/or inhibit the inflammatory state, which has the anti-inflammatory effect.

Example 7: Gene Test

A. Material and Apparatus:

1. Cell line: Human keratinocytes, purchased from AddexBio, with a cell number of T0020001, hereinafter referred to as HaCaT cells.

2. Cell culture medium: Dulbecco's modified Eagle's medium (purchased from Gibco, product No. 12100-038), with 1% antibiotics (purchased from Invivogen, product No. ant-mpp) and 10% fetal bovine serum (purchased from Gibco, product No. 10437-028) added.

3. RNA extraction kit, purchased from Geneaid, product No. DR100.

4. SuperScript® III reverse transcriptase, purchased from Invitrogen, product No. 18080-044.

5. ABI StepOnePlus™ Real-Time PCR system, purchased from Thermo Fisher Scientific.

6. KAPA SYBR FAST qPCR Kit (2×), purchased from KAPA Biosystems, product No. KK4600.

B. Test Procedure:

1. The HaCaT cells were inoculated into a 6-well culture plate containing 2 mL of the cell culture medium per well in a density of $1×10^5$ cells per well, and cultured at 37° C. for 24 h. In this case, the HaCaT cells were divided into two test groups: a blank group and an experimental group. The test for each group was repeated for three times.

2. The culture medium in each group was replaced with an experiment medium after 24 hours of culture, and then cultured at 37° C. for 24 h. The experiment medium in the blank group was the cell culture medium without the sample. The experiment medium in the experimental group was the cell culture medium containing 0.125% (v/v) of the *Lacticaseibacillus Paracasei* TCI077 sample prepared in Example 2.

relative to the RNA expression of the same gene in the blank group. In this case, the mRNA expression of the gene can be indirectly quantified by the quantitative real-time reverse transcription polymerase chain reaction of cDNA, to deduce the expression of the protein encoded by the gene. In the $2^{-\Delta\Delta Ct}$ method, a cycle threshold (Ct) of the TATA-box binding protein (TBP) gene was used as a cycle threshold (Ct) of a reference gene for internal control. The fold change was calculated according to the following formula:

$$\Delta Ct = Ct_{\text{target gene of experimental group/target gene of blank group}} - Ct_{TBP}$$

$$\Delta\Delta Ct = \Delta Ct_{\text{target gene of experimental group}} - \Delta Ct_{\text{target gene of blank group}}$$

$$\text{Fold change} = 2^{-\Delta\Delta Ct \text{ average}}$$

TABLE 2

| Target gene | Primer name | Sequence No. | Sequence |
|---|---|---|---|
| HAS2 | HAS2-F | SEQ ID NO: 2 | AAGAACAACTTCCACGAAAAGGG |
|  | HAS2-R | SEQ ID NO: 3 | GGCTGGGTCAAGCATAGTGT |
| HAS3 | HAS3-F | SEQ ID NO: 4 | CGCAGCAACTTCCATGAGG |
|  | HAS3-R | SEQ ID NO: 5 | AGTCGCACACCTGGATGTAGT |
| GBA | GBA-F | SEQ ID NO: 6 | TCCAGTTGCACAACTTCAGC |
|  | GBA-R | SEQ ID NO: 7 | TTGTGCTCAGCATAGGCATC |
| AQP3 | AQP3-F | SEQ ID NO: 8 | GGGGAGATGCTCCACATCC |
|  | AQP3-R | SEQ ID NO: 9 | AAAGGCCAGGTTGATGGTGAG |
| FLG-F | FLG-F-F | SEQ ID NO: 10 | GGCAAATCCTGAAGAATCCA |
|  | FLG-F-R | SEQ ID NO: 11 | TGCTTTCTGTGCTTGTGTCC |
| TGM1 | TGM1-F | SEQ ID NO: 12 | GCACCACACAGACGAGTATGA |
|  | TGM1-R | SEQ ID NO: 13 | GGTGATGCGATCAGAGGATTC |
| KRT1 | KRT1-F | SEQ ID NO: 14 | AGAGTGGACCAACTGAAGAGT |
|  | KRT1-R | SEQ ID NO: 15 | ATTCTCTGCATTTGTCCGCTT |
| KRT10 | KRT10-F | SEQ ID NO: 16 | ATGTCTGTTCGATACAGCTCAAG |
|  | KRT10-R | SEQ ID NO: 17 | CTCCACCAAGGGAGCCTTTG |
| KRT14 | KRT14-F | SEQ ID NO: 18 | TTCTGAACGAGATGCGTGAC |
|  | KRT14-R | SEQ ID NO: 19 | GCAGCTCAATCTCCAGGTTC |

3. The HaCaT cells in each group were collected after 24 hours of culture. Then, RNA in the HaCaT cells in each group was extracted using the RNA extraction kit.

4. 2000 ng of extracted RNA in each group was used as a template, and the extracted RNA was reverse-transcribed into corresponding cDNA by the SuperScript® III reverse transcriptase.

5. The cDNA of each group was subjected to the quantitative real-time reverse transcription polymerase chain reaction with KAPA SYBR FAST qPCR Kit (2×) and primer pairs in Table 2 by using the ABI StepOnePlus™ Real-Time PCR system, to observe the expression of various target genes of the HaCaT cells in the blank group and the experimental group and melting curves thereof. The apparatus setting conditions for the quantitative real-time reverse transcription polymerase chain reaction were set to reaction at 95° C. for 20 s, reaction at 95° C. for 3 s, and reaction at 60° C. for 30 s, and repeating for 40 cycles.

6. The relative expression level of the target genes was determined by the $2^{-\Delta\Delta Ct}$ method. The relative expression level was defined as the fold change of the RNA expression of a target gene in the experimental group or the blank group C. Test Results:

The relative target gene expression level of each group was calculated according to the following formula: relative target gene expression level=(target gene expression of each group/target gene expression of blank group).

Statistically significant differences between the results of the blank group and the experimental group were analyzed by the student t-test. In the figure, "*" means that the p value was less than 0.05 when compared with the blank group, "" means that the p value was less than 0.01 when compared with the blank group, and "*" means that the p value was less than 0.001 when compared with the blank group.

Figure 5:
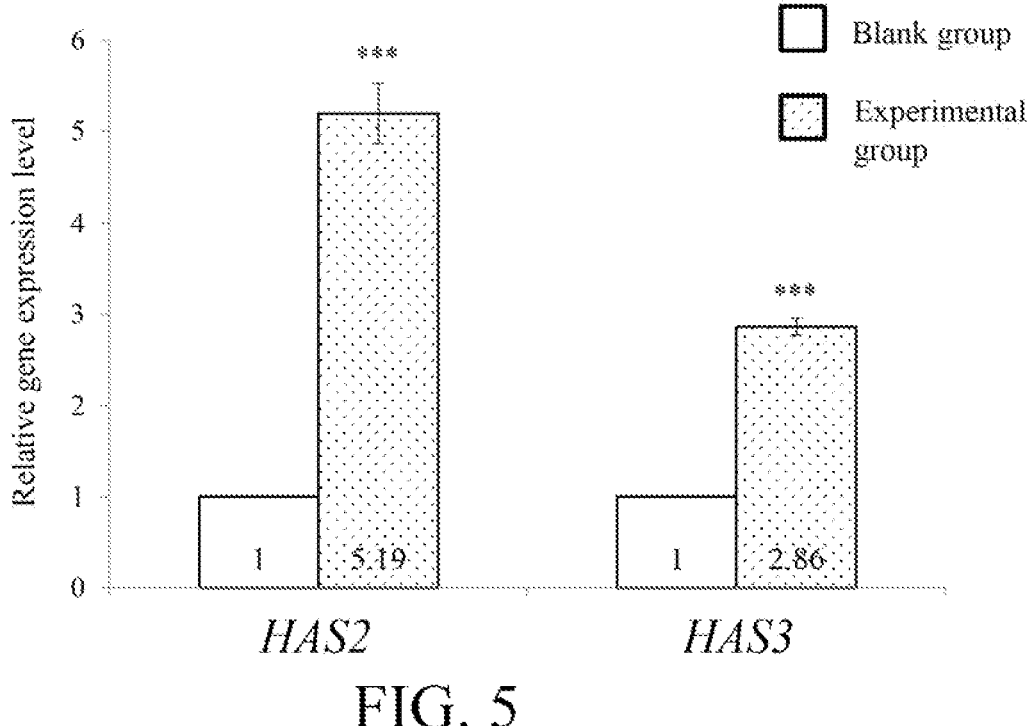
FIG. 5 is a bar chart showing the relative gene expression level after treated by a *Lacticaseibacillus Paracasei* TCI077 sample in accordance with some embodiments of the present disclosure.

Refer to FIG. 5. The cells in the blank group were not treated with the sample, so the test results of the blank group represented the performance of the cells under a normal physiological metabolism condition. In this case, when the relative HAS2 gene expression level and the relative HAS3 gene expression level of the blank group were both set to 1, the relative HAS2 gene expression level of the experimental group was 5.19, and the relative HAS3 gene expression level of the experimental group was 2.86. To be specific, compared with the blank group, the relative HAS2 gene expression level of the experimental group was significantly increased by about 419% after the cells in the experimental group were treated with the *Lacticaseibacillus Paracasei* TCI077 sample. Compared with the blank group, the relative HAS3 gene expression level of the experimental group was significantly increased by about 186% after the cells in the experimental group were treated with the *Lacticaseibacillus Paracasei* TCI077 sample.

It can be learned from the test results that the *Lacticaseibacillus Paracasei* TCI077 sample can increase the expression of the HAS2 and HAS3 genes of the keratinocytes. The HAS2 and H.4S3 genes are responsible for producing hyaluronan synthase, which is involved in the synthesis of hyaluronic acid. Hyaluronic acid is the main component of the extracellular matrix. In other words, as verified by the experiment, the *Lacticaseibacillus Paracasei* TCI077 or the metabolites thereof has the effect of enhancing the synthesis of hyaluronic acid by keratinocytes and increasing the content of hyaluronic acid in keratinocytes. Since hyaluronic acid can preserve water in the extracellular matrix, the *Lacticaseibacillus Paracasei* TCI077 or the metabolites thereof has the effect of improving skin moisture. The *Lacticaseibacillus Paracasei* TCI077 or the metabolites thereof has the effect of promoting the synthesis of substances related to water retention, promoting the synthesis of hyaluronic acid, and increasing the content of hyaluronic acid. Hyaluronic acid can also lubricate joints and promote wound healing and tissue repair.

Figure 6:
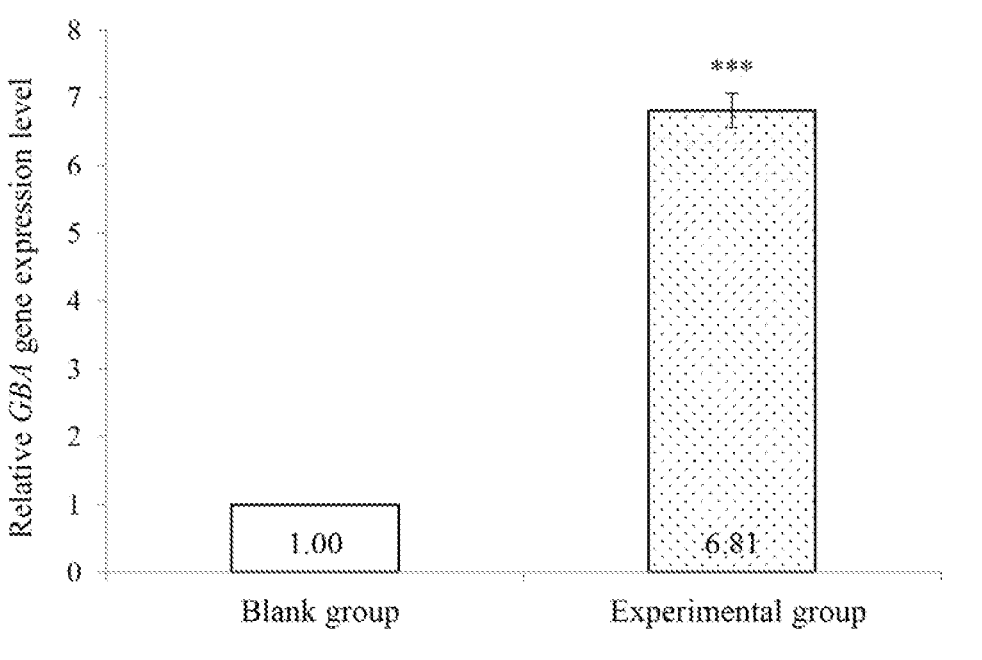
FIG. 6 is a bar chart showing the relative GBA gene expression level after treated by a *Lacticaseibacillus Paracasei* TCI077 sample in accordance with some embodiments of the present disclosure.

Refer to FIG. 6. The cells in the blank group were not treated with the sample, so the test results of the blank group represented the performance of the cells under a normal physiological metabolism conditions. In this case, when the relative GBA gene expression level of the blank group was set to 1, the relative GBA gene expression level of the experimental group was 6.81. To be specific, compared with the blank group, the relative GBA gene expression level of the experimental group was significantly increased by about 581% after the cells in the experimental group were treated with the *Lacticaseibacillus Paracasei* TCI077 sample.

It can be learned from the test results that the *Lacticaseibacillus Paracasei* TCI077 sample can increase the expression of the GBA gene of the keratinocytes. The GBA gene is responsible for producing enzymes that help break down large molecules of glucocerebroside into glucose and ceramides. Ceramide is the main component of the stratum corneum, and stabilizes the space between cells together with cholesterol and fatty acids, to form an impermeable layer that prevents excessive water loss through evaporation. In other words, as verified by the experiment, the *Lacticaseibacillus Paracasei* TCI077 or the metabolites thereof has the effect of enhancing the production of ceramides by keratinocytes and increasing the content of ceramides in keratinocytes. Since ceramides can form a protective layer to lock moisture, the *Lacticaseibacillus Paracasei* TCI077 or the metabolites thereof has the effect of improving skin moisture. The *Lacticaseibacillus Paracasei* TCI077 or the metabolites thereof has the effect of promoting the synthesis of substances related to water retention, promoting the production of ceramides, and increasing the content of ceramides. Moreover, since ceramides largely exist in the stratum corneum of the skin, ceramides can also maintain the skin structure, strengthen the skin barrier, and improve the skin stability.

Figure 7:
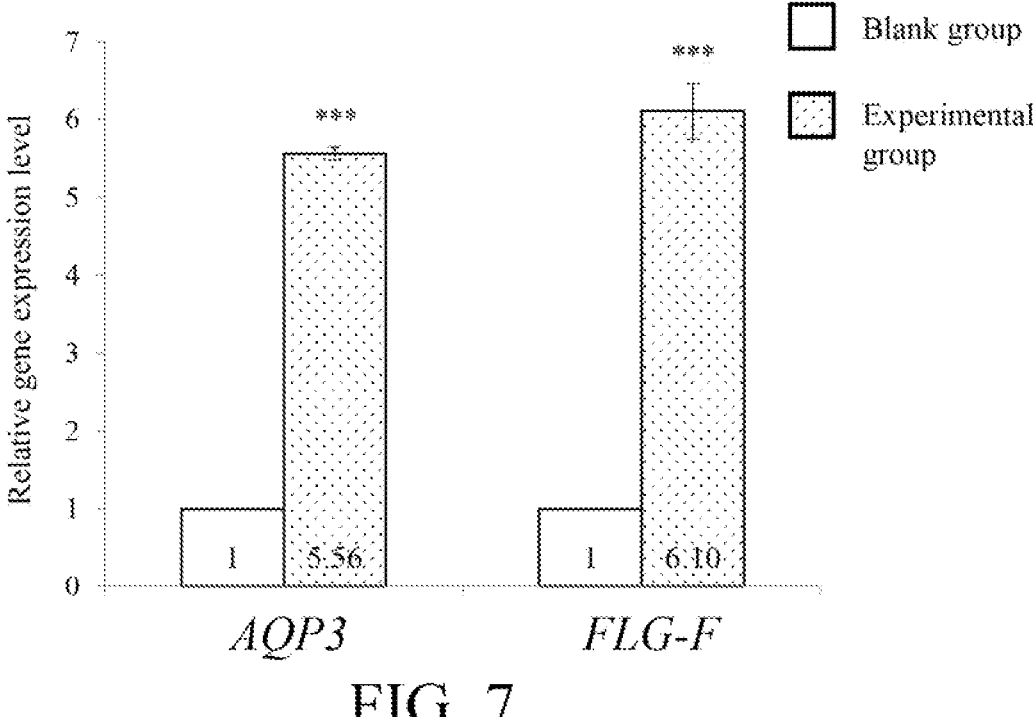
FIG. 7 is a bar chart showing the relative gene expression level after treated by a *Lacticaseibacillus Paracasei* TCI077 sample in accordance with some embodiments of the present disclosure.

Refer to FIG. 7. The cells in the blank group were not treated with the sample, so the test results of the blank group represented the performance of the cells under anormal physiological metabolism condition. In this case, when the relative AQP3 gene expression level and the relative FLG-F gene expression level of the blank group were both set to 1, the relative AQP3 gene expression level of the experimental group was 5.56, and the relative FLG-F gene expression level of the experimental group was 6.10. To be specific, compared with the blank group, the relative AQP3 gene expression level of the experimental group was significantly increased by about 456% after the cells in the experimental group were treated with the *Lacticaseibacillus Paracasei* TCI077 sample. Compared with the blank group, the relative FLG-F gene expression level of the experimental group was significantly increased by about 510% after the cells in the experimental group were treated with the *Lacticaseibacillus Paracasei* TCI077 sample.

It can be learned from the test results that the *Lacticaseibacillus Paracasei* TCI077 sample can increase the expression of the AQP3 gene of the keratinocytes. The AQP3 gene is responsible for producing aquaporin 3, which is a transporter protein on cell membranes that transports small molecules such as water, glycerol, and urea across cell membranes, and is involved in skin hydration, strengthening the skin barrier, and promoting wound healing, to maintain normal skin morphology and function. In other words, as verified by the experiment, the *Lacticaseibacillus Paracasei* TCI077 or the metabolites thereof has the effect of increasing the content of aquaporins in keratinocytes, promoting the transportation of water across the cell membranes, increasing the water content of the skin, strengthening the skin barrier, and promoting wound healing. The *Lacticaseibacillus Paracasei* TCI077 or the metabolites thereof has the effect of promoting the production of natural moisturizing factors and increasing the content of aquaporins.

It can be learned from the test results that the *Lacticaseibacillus Paracasei* TCI077 sample can increase the expression of the FLG-F gene of the keratinocytes. The FLG-F gene is responsible for producing filaggrins that build the skin barrier and produce natural moisturizing factors (NMFs). The NMF plays an important role in the water retention function of the stratum corneum. In other words, as verified by the experiment, the *Lacticaseibacillus Paracasei* TCI077 or the metabolites thereof has the effect of increasing the content of filaggrins in keratinocytes and strengthening the skin barrier. The *Lacticaseibacillus Paracasei* TCI077 or the metabolites thereof has the effect of increasing the content of natural moisturizing factors (NMFs) in keratinocytes and improving the water retention of the skin. The *Lacticaseibacillus Paracasei* TCI077 or the metabolites thereof has the effect of increasing the content of filaggrins and increasing the content of natural moisturizing factors (NMFs).

Figure 8:
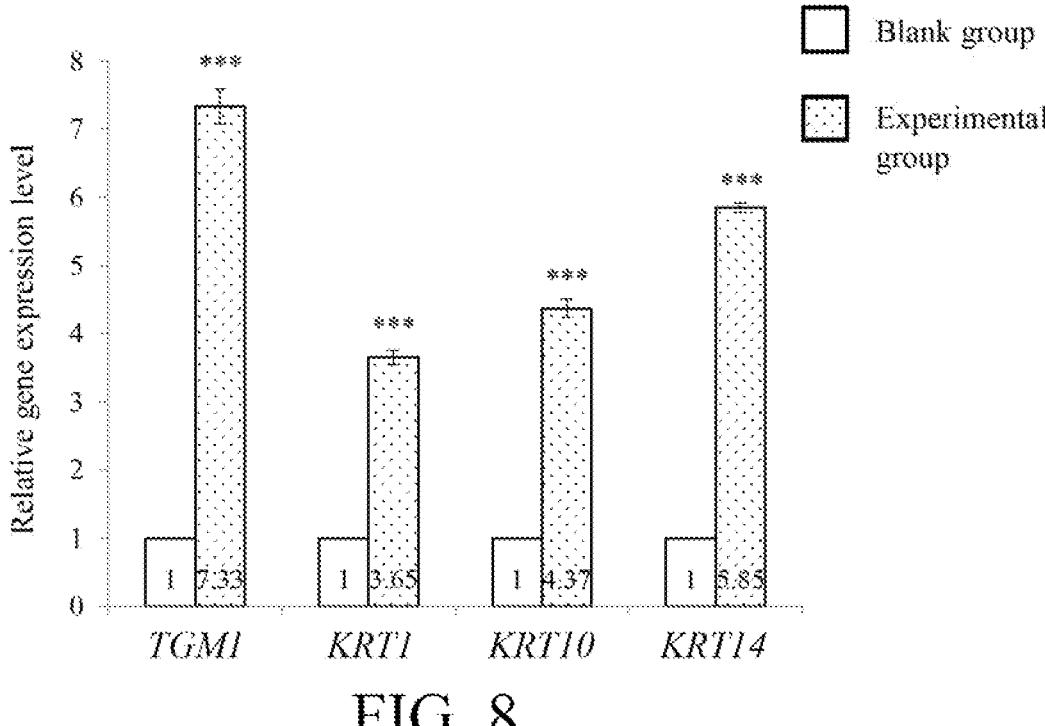
FIG. 8 is a bar chart showing the relative gene expression level after treated by a *Lacticaseibacillus Paracasei* TCI077 sample in accordance with some embodiments of the present disclosure.

Refer to FIG. 8. The cells in the blank group were not treated with the sample, so the test results of the blank group represented the performance of the cells under anormal physiological metabolism condition. In this case, when the relative TGM1 gene expression, the relative KRT1 gene expression, the relative KRT10 gene expression, and the relative KRT14 gene expression level of the blank group were all set to 1, the relative TGM1 gene expression level of the experimental group was 7.33, the relative KRT1 gene expression level of the experimental group was 3.65, the relative KRT10 gene expression level of the experimental group was 4.37, and the relative KRT14 gene expression level of the experimental group was 5.85. To be specific, compared with the blank group, the relative TGM1 gene expression level of the experimental group was significantly increased by about 633% after the cells in the experimental group were treated with the *Lacticaseibacillus Paracasei* TCI077 sample. Compared with the blank group, the relative KR71 gene expression level of the experimental group was significantly increased by about 265% after the cells in the experimental group were treated with the *Lacticaseibacillus Paracasei* TCI077 sample. Compared with the blank group, the relative KRT10 gene expression level of the experimental group was significantly increased by about 337% after the cells in the experimental group were treated with the *Lacticaseibacillus Paracasei* TCI077 sample. Compared with the blank group, the relative KRT4 gene expression level of the experimental group was significantly increased by about 485% after the cells in the experimental group were treated with the *Lacticaseibacillus Paracasei* TCI077 sample.

It can be learned from the test results that the *Lacticaseibacillus Paracasei* TCI077 sample can increase the expression of the TGM1, KRT1, KRT70, and KRT14 genes of the keratinocytes. The TGM1 gene is responsible for producing enzymes involved in the formation of the cornified cell envelope, providing strength and stability for the epidermis to form a protective barrier. The KRT gene is responsible for producing keratins. These keratin, together with other keratins, form the cytoskeleton of the epithelial cells, which is the main component of the skin, is important for the formation of the natural barrier of the skin, and can maintain the structure of keratinocytes of the skin. In addition, the compactness of keratinocytes depends on keratins. In other words, as verified by the experiment, the *Lacticaseibacillus Paracasei* TCI077 or the metabolites thereof has the effect of increasing the content of keratins in keratinocytes, strengthening the skin barrier, strengthening the skin structure, and reducing water loss. The *Lacticaseibacillus Paracasei* TCI077 or the metabolites thereof has the effect of improving the compactness, strength, and stability of keratinocytes.

Example 8: Human Subject Test

A. Test Procedure:

Nine adult subjects from the ages 20 to 50 with oily skin were assigned to take one test capsule daily for four weeks (that is, 28 days). The test capsule contains bacterial particulates. The bacterial particulate comprises live *Lacticaseibacillus Paracasei* TCI077, first covering layer, second covering layer and third covering layer. The first covering layer is in-between a cell membrane and a cell wall of the live *Lacticaseibacillus Paracasei* TCI077 and the live *Lacticaseibacillus Paracasei* TCI077 is dispersed in the second covering layer. The third covering layer is outside and covering the second covering layer. The first covering layer comprises lactose, the second covering layer comprises maltodextrin, and the third covering layer comprises skim milk powder. The test capsule contains $5 \times 10^9$ CFU of live *Lacticaseibacillus Paracasei* TCI077. In addition, the subjects underwent skin detection and blood detection before administration (at week 0), after 14 days of administration (at week 2), and after 28 days of administration (at week 4). The subjects filled in a questionnaire after 28 days of administration (at week 4).

The skin detection based on different skin detection items, includes recording values of facial skin using corresponding apparatuses and measurement methods, and taking photos of the skin before and after administration. The skin detection items include the skin water content, the skin oil content, and the degree of skin wrinkles. Moreover, the temperature and humidity of test regions where the subjects were located were the same when detection was performed at week 0, week 2, and week 4, to minimize the effect of external factors such as temperature and humidity on the skin.

The skin water content was measured on the facial skin of the same subject before and after administration by using a skin water content measuring probe Corneometer® CM825 (C+K Multi Probe Adapter System, Germany) purchased from Courage+Khazaka electronic, Germany. The measuring probe was used based on the principle of capacitance. When the water content changes, the capacitance value of the skin also changes. Therefore, the capacitance value of the skin may be measured to obtain a value that represents the water content of the skin (hereinafter referred to as the skin water content value). In this case, a higher skin water content value indicates a higher skin water content. The relative skin water content was then calculated according to the following formula: relative skin water content (%) (skin water content value of each group/skin water content value before administration)×100%.

The skin oil content was measured on the facial skin of the same subject before and after administration by using a skin oil content measuring probe Sebumeter® SM815 (C+K Multi Probe Adapter System, Germany) purchased from Courage+Khazaka electronic, Germany. This probe was used based on the principle of photometers. The skin oil was absorbed by test paper in the probe, and then a value that can represent the oil content of the skin (hereinafter referred to as the skin oil content value) was calculated based on the transmittance of light through the test paper. In this case, a higher skin oil content value indicates a higher skin oil content. The relative skin oil content was then calculated according to the following formula: relative skin oil content (%)=(skin oil content value of each group/skin oil content value before administration)×100%.

The degree of skin wrinkles was measured on the facial skin of the same subject before and after administration by using a VISIA Complexion Analysis System purchased from Canfield scientific, USA. By using the VISIA Complexion Analysis System, photos of the facial skin were taken through a high-resolution camera lens, and the length and depth of wrinkles can be analyzed and calculated based on changes in skin shadows by irradiating the skin with visible light (white light) to obtain a value that can represent the degree of skin wrinkles (hereinafter referred to as the skin wrinkle degree value). In this case, a higher skin wrinkle degree value indicates more serious skin wrinkles. The relative skin wrinkle degree was then calculated according to the following formula: relative skin wrinkle degree (%)= (skin wrinkle degree value of each group/skin wrinkle degree value before administration)×100%.

The blood detection was conducted by Lezen Clinical Laboratory (Taiwan) to determine the change of neutrophil count in the blood of the subject before and after administration.

The questionnaire survey was conducted by the subjects to fill in the questionnaire for self-assessment after 28 days of administration. The questionnaires are shown in Table 3, Table 4, and Table 5 below.

As shown in Table 3 below, the subjects self-assessed their skin condition. Ater the self-assessment, each subject chose one of the four options: strong feeling, slightly feeling, no feeling, and more serious.

TABLE 3

| Skin condition | Strong feeling | Slight feeling | No feeling | More serious |
|---|---|---|---|---|
| After 28 days of administration, fine wrinkles of the skin are reduced | | | | |
| After 28 days of administration, the skin feels tender and smooth | | | | |
| After 28 days of administration, dry, itchy, and red skin is relieved | | | | |
| After 28 days of administration, dryness and dehydration of the skin are relieved | | | | |
| After 28 days of administration, the skin feels less oily | | | | |

As shown in Table 4 below, the subjects self-assessed their defecation frequency and duration required for defecation. After the self-assessment, each subject chose one of the following options.

TABLE 4

| Defecation frequency | More than twice a day | Once a day | Once every two days |
|---|---|---|---|
| How often did you defecate before administration? | | | |
| How often did you defecate after 28 days of administration? | | | |
| Duration required for defecation | <5 min | 10-20 min | >20 min |
| How long did you take to defecate in the toilet before administration? | | | |
| How long did you take to defecate in the toilet after 28 days of administration? | | | |

As shown in Table 5 below, the subjects self-assessed their defecation condition. After the self-assessment, each subject chose one of the five options: strongly agree, agree, average, disagree, and strongly disagree.

TABLE 5

| Defecation condition | Strongly agree | Agree | Average | Disagree | Strongly disagree |
|---|---|---|---|---|---|
| Cleaner and smoother | | | | | |
| Less painful | | | | | |
| Easier | | | | | |
| Softer feces | | | | | |

B. Test Results:

Statistically significant differences between the results at week 0 and at the other weeks were analyzed by the student t-test. In the figure, "*" means that the p value was less than 0.05 when compared with week 0, "" means that the p value was less than 0.01 when compared with week 0, and "*" means that the p value was less than 0.001 when compared with week 0.

Figure 9:
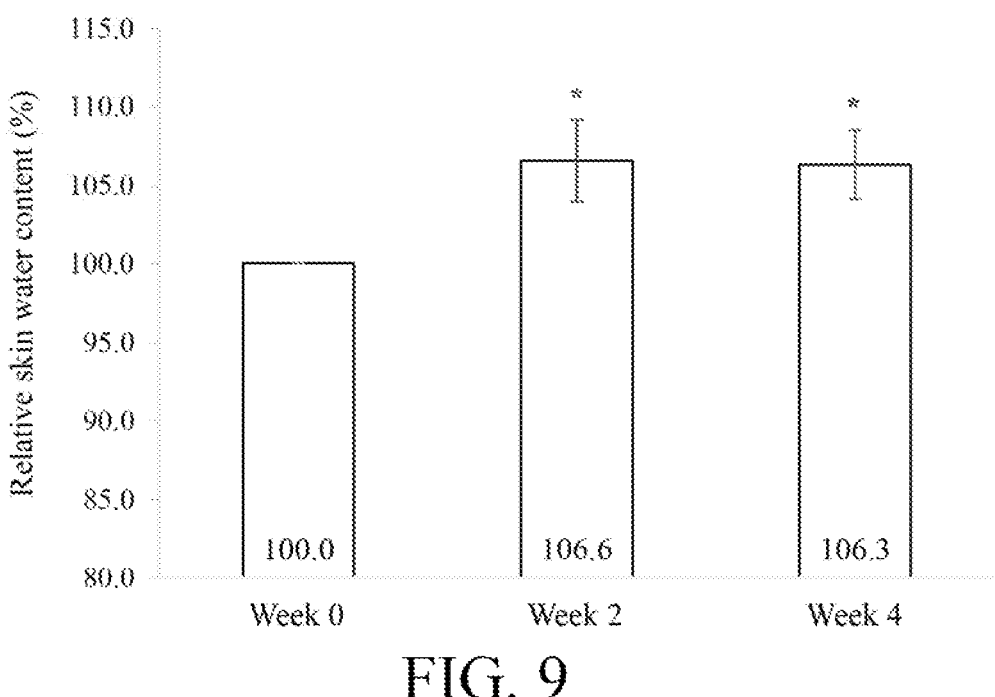
FIG. 9 is a bar chart showing the relative skin water content in human subjects at week 0, week 2, and week 4 after ingesting a composition including *Lacticaseibacillus Paracasei* TCI077 in accordance with some embodiments of the present disclosure.

Refer to FIG. 9. The skin water content value measured for each of the nine subjects before administration was considered as 100% of relative skin water content. In this case, the relative skin water content at week 2 (that is, after two weeks of continuous administration of the test capsule) was 106.6%, and the relative skin water content at week 4 (that is, after four weeks of continuous administration of the test capsule) was 106.3%. In other words, compared with the relative skin water content before administration, the relative skin water content of these subjects after two weeks of continuous administration of live *Lacticaseibacillus Paracasei* TCI077 can be significantly increased by 6.6%, and the relative skin water content of these subjects after four weeks of continuous administration of live *Lacticaseibacillus Paracasei* TCI077 can be significantly increased by 6.3%. In addition, the percentage of improvement was 77.8% (seven subjects). Therefore, the live *Lacticaseibacillus Paracasei* TCI077 can indeed increase the skin water content. In other words, as verified by the experiment, the *Lacticaseibacillus Paracasei* TCI077 or the metabolites thereof has the effect of improving skin moisture.

Figure 10:
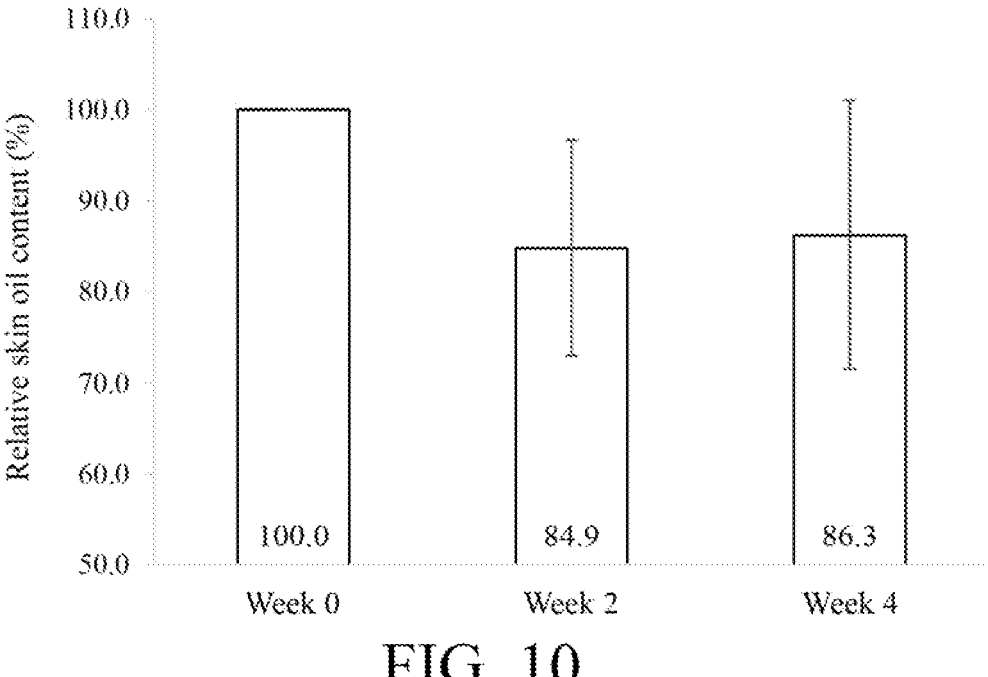
FIG. 10 is a bar chart showing the relative skin oil content in human subjects at week 0, week 2, and week 4 after ingesting a composition including *Lacticaseibacillus Paracasei* TCI077 in accordance with some embodiments of the present disclosure.

Refer to FIG. 10. The skin oil content value measured for each of the nine subjects before administration was considered as 100% of relative skin oil content. In this case, the relative skin oil content at week 2 (that is, after two weeks of continuous administration of the test capsule) was 84.9%, and the relative skin oil content at week 4 (that is, after four weeks of continuous administration of the test capsule) was 86.3%. In other words, compared with the relative skin oil content before administration, the relative skin oil content of these subjects after two weeks of continuous administration of live *Lacticaseibacillus Paracasei* TCI077 can be reduced by 15.1%, and the relative skin oil content of these subjects after four weeks of continuous administration of live *Lacticaseibacillus Paracasei* TCI077 can be reduced by 13.7%. In addition, the percentage of improvement was 66.7% (six subjects). Therefore, the live *Lacticaseibacillus Paracasei* TCI077 can indeed reduce the skin oil content. In other words, as verified by the experiment, the *Lacticaseibacillus Paracasei* TCI077 or the metabolites thereof has the effect of reducing skin oil content.

Since the *Lacticaseibacillus Paracasei* TCI077 or the metabolites thereof can simultaneously increase the skin water content and reduce the skin oil content, the *Lacticaseibacillus Paracasei* TCI077 or the metabolites thereof has the effect of improving skin oil-water balance and regulating oil-water balance. Since skin oil-water imbalance leads to the production of acne and/or pimples, the *Lacticaseibacillus Paracasei* TCI077 or the metabolites thereof has the effect of reducing the formation of acne and/or pimples.

Figure 11:
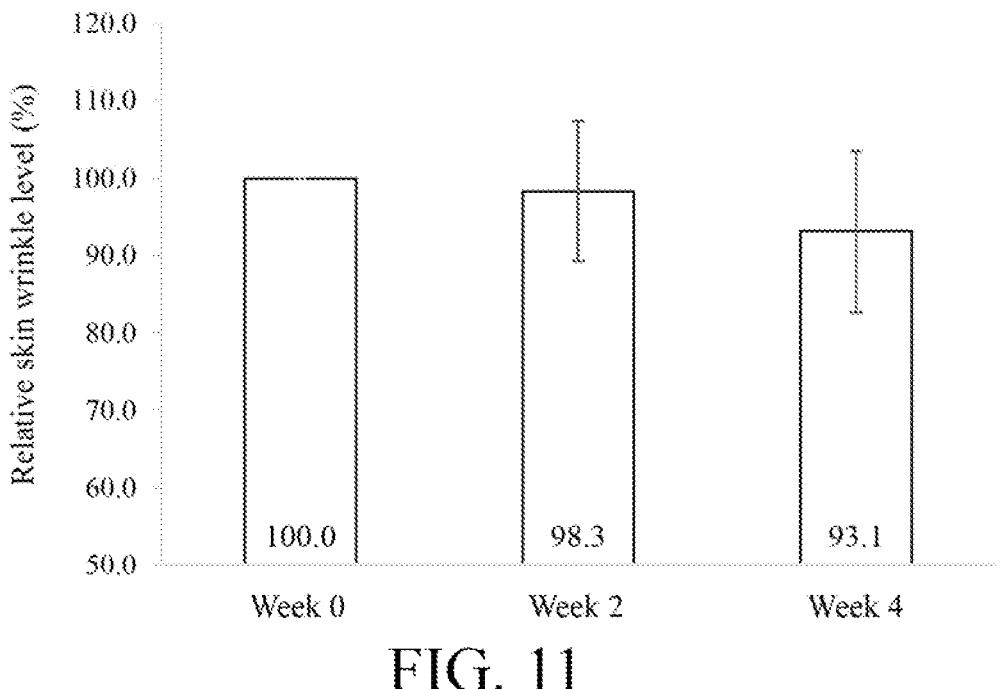
FIG. 11 is a bar chart showing the relative skin wrinkle level in human subjects at week 0, week 2, and week 4 after ingesting a composition including *Lacticaseibacillus Paracasei* TCI077 in accordance with some embodiments of the present disclosure.

Refer to FIG. 11. The skin wrinkle degree value measured for each of the nine subjects before administration was considered as 100% of relative skin wrinkle degree. In this case, the relative skin wrinkle degree at week 2 (that is, after two weeks of continuous administration of the test capsule) was 98.3%, and the relative skin wrinkle degree at week 4 (that is, after four weeks of continuous administration of the test capsule) was 93.1%. In other words, compared with the relative skin wrinkle degree before administration, the relative skin wrinkle degree of these subjects after two weeks of continuous administration of live *Lacticaseibacillus Paracasei* TCI077 can be reduced by 1.7%, and the relative skin wrinkle degree of these subjects after four weeks of continuous administration of live *Lacticaseibacillus Paracasei* TCI077 can be reduced by 6.9%. In addition, the percentage of improvement was 66.7% (six subjects). Therefore, the live *Lacticaseibacillus Paracasei* TCI077 can indeed reduce skin wrinkles. In other words, as verified by the experiment, the *Lacticaseibacillus Paracasei* TCI077 or the metabolites thereof has the effect of reducing skin wrinkles and smoothing out fine wrinkles of the skin.

Figure 12:
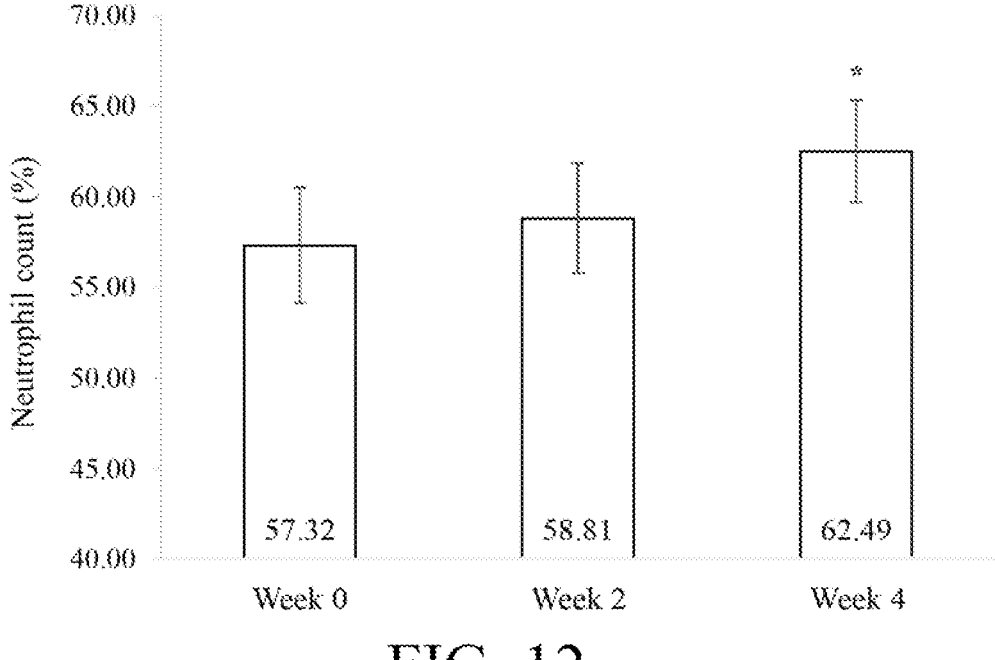
FIG. 12 is a bar chart showing the neutrophil count in blood in human subjects at week 0, week 2, and week 4 after ingesting a composition including *Lacticaseibacillus Para-casei* TCI077 in accordance with some embodiments of the present disclosure.

Refer to FIG. 12. The neutrophil count at week 0 was about 57.32%, the neutrophil count at week 2 (that is, after two weeks of continuous administration of the test capsule) was about 58.81%, and the neutrophil count at week 4 (that is, after four weeks of continuous administration of the test capsule) was about 62.49%. In other words, compared with the neutrophil count before administration, the neutrophil count of these subjects after two weeks of continuous administration of live *Lacticaseibacillus Paracasei* TCI077 can be increased by 2.6%, and the neutrophil count of these subjects after four weeks of continuous administration of live *Lacticaseibacillus Paracasei* TCI077 can be significantly increased by 9.0%. In addition, the percentage of improvement was 77.8% (seven subjects). Therefore, the live *Lacticaseibacillus Paracasei* TCI077 can indeed increase the neutrophil counts and boost immunity. In other words, as verified by the experiment, the *Lacticaseibacillus Paracasei* TCI077 or the metabolites thereof has the effect of increasing neutrophil counts and boosting immunity.

Figure 13:
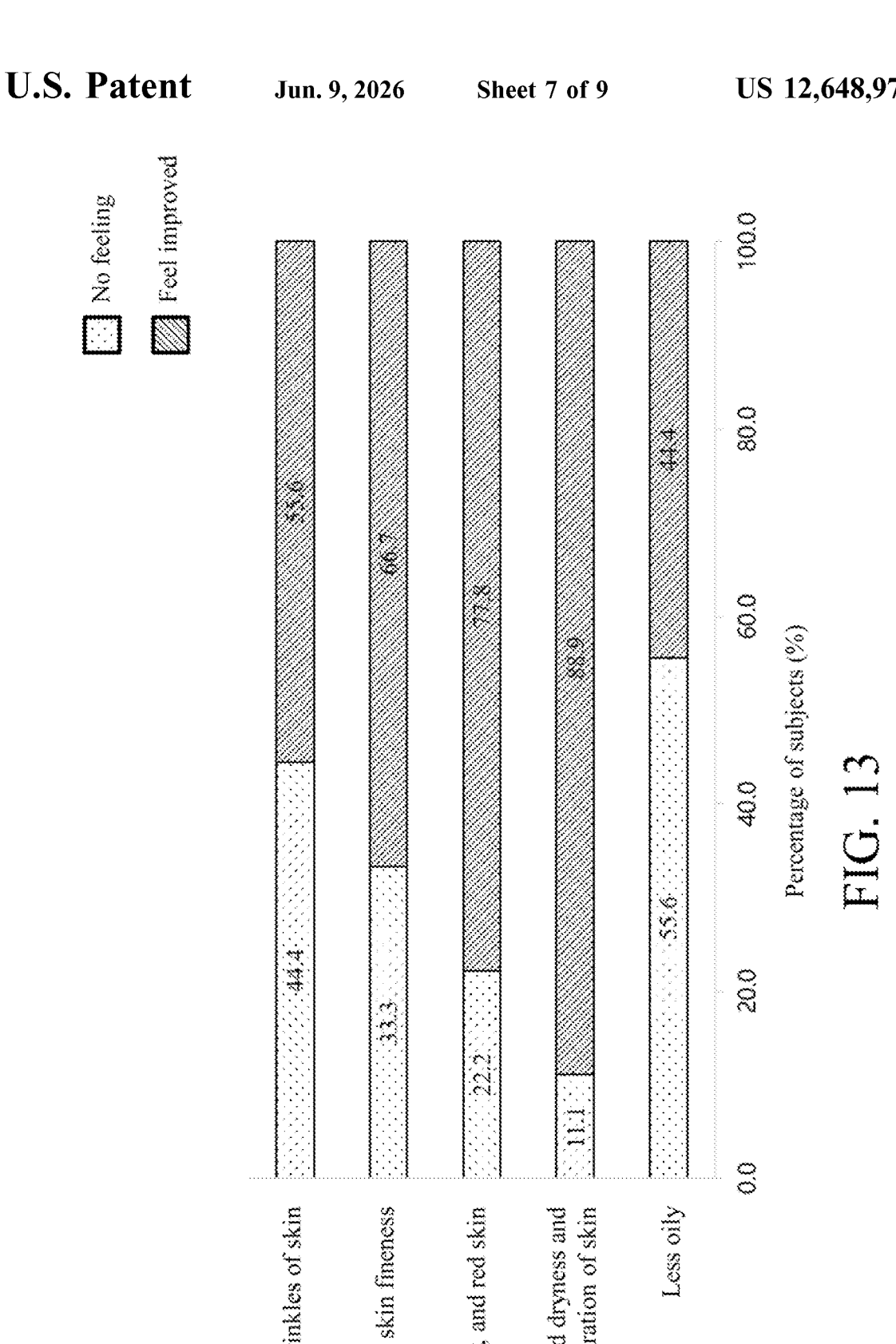
FIG. 13 is a horizontal bar chart showing the percentage of subjects of a questionnaire on self-assessment of skin condition in a human subject test.

Refer to FIG. 13. At week 4, 44.4% of the subjects (four subjects) felt that no fine wrinkles of the skin were reduced while 55.6% of the subjects (five subjects) felt that fine wrinkles of the skin were reduced. 33.3% of the subjects (three subjects) felt that no skin fineness was improved while 66.7% of the subjects (six subjects) felt that skin fineness was improved. 22.2% of the subjects (two subjects) felt that no dry, itchy, and red skin was relieved while 77.8% of the subjects (seven subjects) felt that dry, itchy, and red skin was relieved. 11.1% of the subjects (one subject) felt that no dryness and dehydration of the skin were relieved while 88.9% of the subjects (eight subjects) felt that dryness and dehydration of the skin were relieved. 55.6% of the subjects (five subjects) felt that the skin was oily while 44.4% of the subjects (four subjects) felt that the skin was less oily. It can be learned that the live *Lacticaseibacillus Paracasei* TCI077 can indeed improve the skin condition including fine wrinkles of the skin, skin fineness, dry, itchy, and red skin, dryness and dehydration of the skin, and skin oil. In other words, as verified by the experiment, the *Lacticaseibacillus Paracasei* TCI077 or the metabolites thereof has the effect of improving the skin condition, including the effect of reducing fine wrinkles of the skin, improving skin fineness, relieving skin dryness, itchiness, and redness, relieving dryness and dehydration of the skin, and reducing skin oil. "Feel improved" indicates a total quantity of the subjects who chose "strong feeling" and "slight feeling" in the questionnaire in Table 3.

Figure 14:
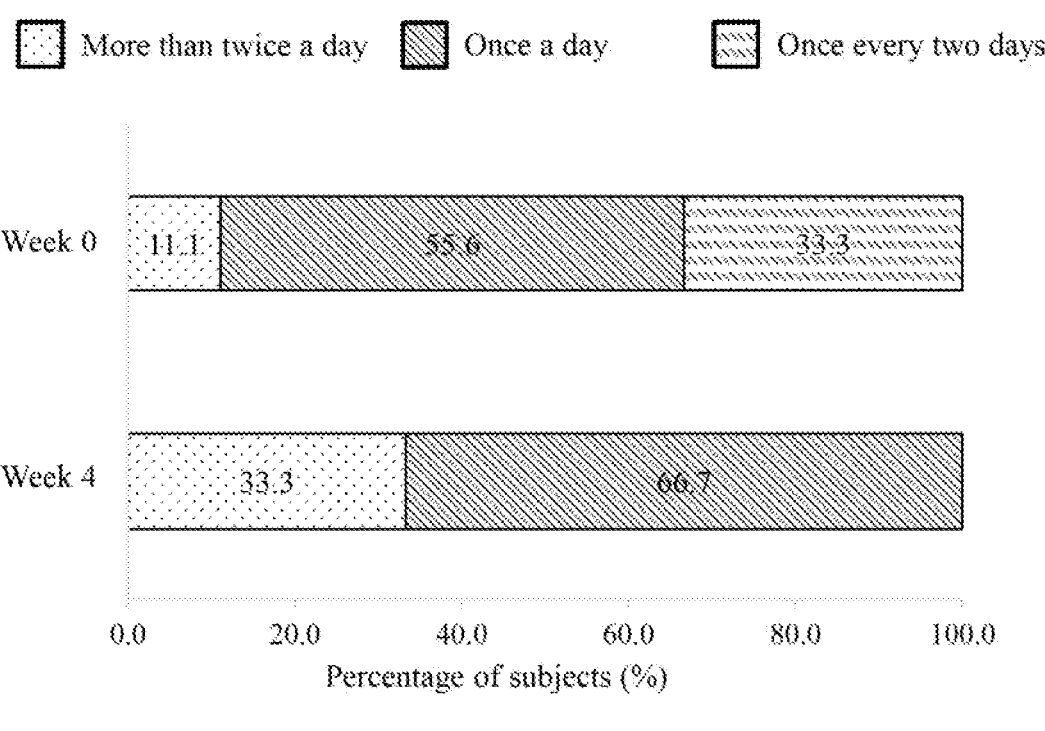
FIG. 14 is a horizontal bar chart showing the percentage of subjects of a questionnaire on self-assessment of defecation frequency in a human subject test.

Refer to FIG. 14. At week 0, 11.1% of the subjects (one subject) defecated more than twice a day, 55.6% of the subjects (five subjects) defecated once a day, and 33.3% of the subjects (three subjects) defecated once every two days. At week 4, 33.3% of the subjects (three subjects) defecated more than twice a day, and 66.7% of the subjects (six subjects) defecated once a day. It can be learned that the live *Lacticaseibacillus Paracasei* TCI077 can indeed increase the defecation frequency and promote defecation to be smooth. In other words, as verified by the experiment, the *Lacticaseibacillus Paracasei* TCI077 or the metabolites thereof has the effect of increasing the defecation frequency and promoting defecation to be smooth.

Figure 15:
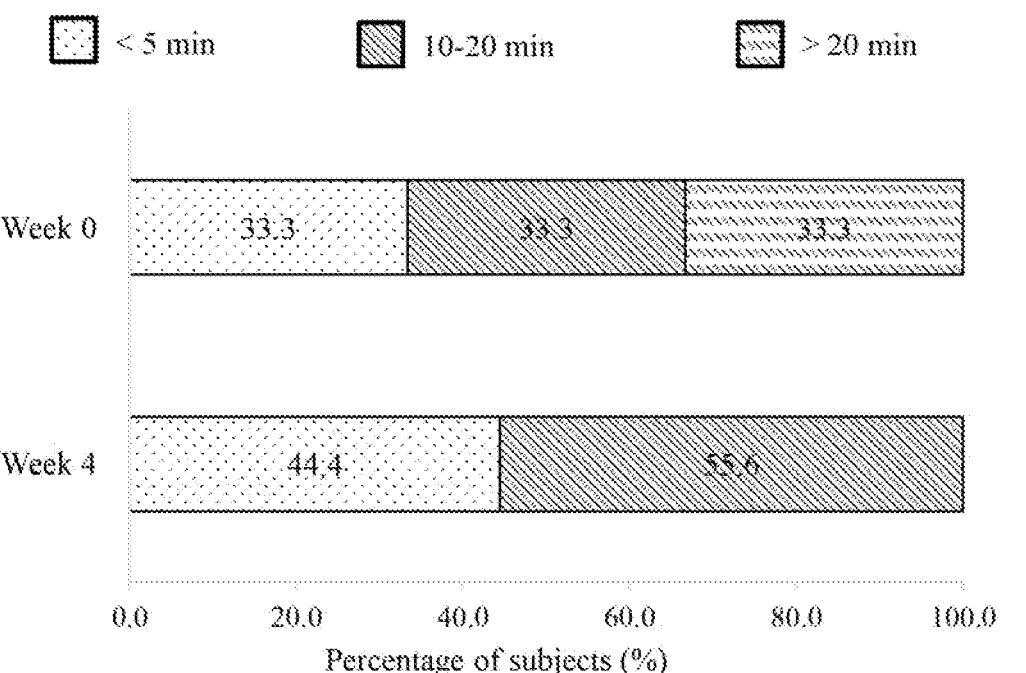
FIG. 15 is a horizontal bar chart showing the percentage of subjects of a questionnaire on self-assessment of duration required for defecation in a human subject test.

Refer to FIG. 15. At week 0, 33.3% of the subjects (three subjects) took less than 5 minutes to defecate, 33.3% of the subjects (three subjects) took 10-20 minutes to defecate, and 33.3% of the subjects (three subjects) took more than 20 minutes to defecate. At week 4, 44.4% of the subjects (four subjects) took less than 5 minutes to defecate, and 55.6% of the subjects (five subjects) took 10-20 minutes to defecate. It can be learned that the live *Lacticaseibacillus Paracasei* TCI077 can indeed reduce the duration required for defecation and promote defecation to be smooth. In other words, as verified by the experiment, the *Lacticaseibacillus Paracasei* TCI077 or the metabolites thereof has the effect of reducing the duration required for defecation and promoting defecation to be smooth.

Figure 16:
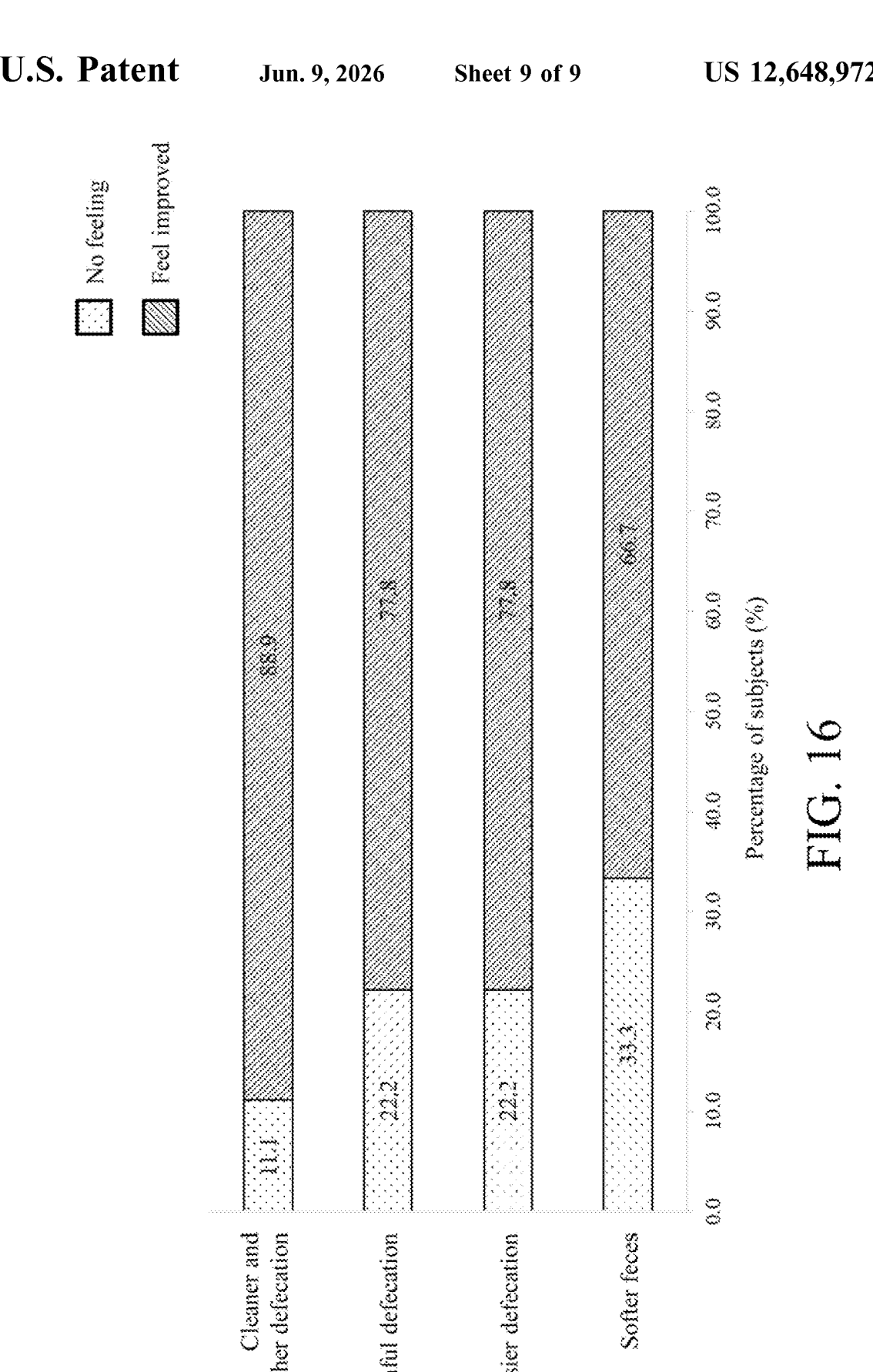
FIG. 16 is a horizontal bar chart showing the percentage of subjects of a questionnaire on perception of defecation condition in a human subject test.

Refer to FIG. 16. At week 4, 11.1% of the subjects (one subject) felt that defecation was not cleaner and smoother while 88.9% of the subjects (eight subjects) felt that defecation was cleaner and smoother. 22.2% of the subjects (two subjects) felt that defecation was painful while 77.8% of the subjects (seven subjects) felt that defecation was less painful. 22.2% of the subjects (two subjects) felt that defecation was not easier while 77.8% of the subjects (seven subjects) felt that defecation was easier. 33.3% of the subjects (three subjects) felt that feces were not softer while 66.7% of the subjects (six subjects) felt that feces were softer. It can be learned that the live *Lacticaseibacillus Paracasei* TCI077 can indeed make defecation cleaner and smoother, less painful, easier, and have softer feces. In other words, as verified by the experiment, the *Lacticaseibacillus Paracasei* TCI077 or the metabolites thereof has the effect of making defecation cleaner and smoother, less painful, easier, and have softer feces. The *Lacticaseibacillus Paracasei* TCI077 or the metabolites thereof has the effect of promoting defecation, improving defecation smoothness, and reducing feces hardness. "Feel improved" indicates a total quantity of the subjects who chose "strongly agree" and "agree" in the questionnaire in Table 5, and "no feeling" indicates a quantity of the subjects who chose "average" in the questionnaire in Table 5.

Based on the above, the *Lacticaseibacillus Paracasei* or the metabolites thereof in any embodiment of the present disclosure has the effect of conditioning skin or boosting immunity. In some embodiments, the *Lacticaseibacillus Paracasei* or the metabolites thereof is suitable for preparing a composition for conditioning skin or boosting immunity. In some embodiments, a method for conditioning skin or boosting immunity includes administering to a subject in need thereof a composition including the *Lacticaseibacillus Paracasei* or the metabolites thereof. In other words, the composition has a function of conditioning skin or boosting immunity. That is to say, the composition administered to an individual can produce the effect of conditioning skin or boosting immunity on the individual. In some embodiments, the *Lacticaseibacillus Paracasei*, the metabolites thereof, or the composition prepared therefrom further has one or more of the following functions: inhibiting acne, inhibiting bacteria, inhibiting inflammation, strengthening skin structure, improving skin moisture, reducing skin wrinkles, relieving skin dryness, itchiness, and redness, boosting immunity, or promoting defecation. In some embodiments, a method for inhibiting acne, inhibiting bacteria, inhibiting inflammation, strengthening skin structure, improving skin moisture, reducing skin wrinkles, relieving skin dryness, itchiness, and redness, boosting immunity, and promoting defecation includes administering to a subject in need thereof a composition including the *Lacticaseibacillus Paracasei* or the metabolites thereof.

What is claimed is:

1. A method for reducing the formation of acne, comprising administering to a subject in need thereof a composition comprising *Lacticaseibacillus paracasei* or supernatant thereof, wherein the *Lacticaseibacillus paracasei* is *Lacticaseibacillus paracasei* TCI077 deposited under an accession number of DSM 34374.

2. The method according to claim 1, wherein the *Lacticaseibacillus paracasei* or the supernatant thereof inhibits the growth of *Propionibacterium acnes.*

3. The method according to claim 1, wherein the *Lacticaseibacillus paracasei* or the supernatant thereof promotes proliferation of skin fibroblasts.

4. The method according to claim 1, wherein the *Lacticaseibacillus paracasei* or the supernatant thereof promotes proliferation of keratinocytes.

5. The method according to claim 1, wherein the *Lacticaseibacillus paracasei* or the supernatant thereof reduces skin oil content.

6. The method according to claim 1, wherein the *Lacticaseibacillus paracasei* or the supernatant thereof improves skin oil-water balance.

7. A method for strengthening skin structure, comprising administering to a subject in need thereof a composition comprising *Lacticaseibacillus paracasei* or supernatant thereof, wherein the *Lacticaseibacillus paracasei* is *Lacticaseibacillus paracasei* TCI077 deposited under an accession number of DSM 34374.

8. The method according to claim 7, wherein the *Lacticaseibacillus paracasei* or the supernatant thereof increases keratins.

9. A method for improving skin moisture, comprising administering to a subject in need thereof a composition comprising *Lacticaseibacillus paracasei* or supernatant thereof, wherein the *Lacticaseibacillus paracasei* is *Lacticaseibacillus paracasei* TCI077 deposited under an accession number of DSM 34374.

10. The method according to claim 9, wherein the *Lacticaseibacillus paracasei* or the supernatant thereof increases hyaluronic acid, ceramides, natural moisturizing factors (NMFs), and/or aquaporins.

11. A method for reducing skin wrinkles, comprising administering to a subject in need thereof a composition comprising *Lacticaseibacillus paracasei* or supernatant thereof, wherein the *Lacticaseibacillus paracasei* is *Lacticaseibacillus paracasei* TCI077 deposited under an accession number of DSM 34374.

12. A method for relieving skin dryness, itchiness, and redness, comprising administering to a subject in need thereof a composition comprising *Lacticaseibacillus paracasei* or supernatant thereof, wherein the *Lacticaseibacillus paracasei* is *Lacticaseibacillus paracasei* TCI077 deposited under an accession number of DSM 34374.

* * * * *

SEQUENCE LISTING

```
Sequence total quantity: 19
SEQ ID NO: 1              moltype = DNA   length = 1155
FEATURE                   Location/Qualifiers
source                    1..1155
                          mol_type = genomic DNA
                          organism = Lacticaseibacillus  Paracasei
SEQUENCE: 1
acaaattttt tgtcacctat agacgagctc gctccctaaa agggttacgc caccggcttc   60
gggtgttaca aactctcatg gtgtgacggg cggtgtgtac aaggcccggg aacgtattca  120
ccgcggcgtg ctgatccgcg attactagcg attccgactt cgtgtaggcg agttgcagcc  180
tacagtccga actgagaatg gctttaagag attagcttga cctcgcggtc tcgcaactcg  240
ttgtaccatc cattgtagca cgtgtgtagc ccaggtcata aggggcatga tgatttgacg  300
tcatccccac cttcctccgg tttgtcaccg gcagtcttac tagagtgccc aactaaatgc  360
tggcaactag tcataagggt tgcgctcgtt gcgggactta acccaacatc tcacgacacg  420
agctgacgac aaccatgcac cacctgtcat tttgcccccg aaggggaaac ctgatctctc  480
aggtgatcaa aagatgtcaa gacctggtaa ggttcttcgc gttgcttcga attaaaccac  540
atgctccacc gcttgtgcgg gcccccgtca attcctttga gtttcaacct tgcggtcgta  600
ctccccaggc ggaatgctta atgcgttagc tgcggcactg aagggcggaa accctccaac  660
acctagcatt catcgtttac ggcatggact accagggtat ctaatcctgt tcgctaccca  720
tgctttcgag cctcagcgtc agttacagac cagacagccg ccttcgccac tggtgttctt  780
ccatatatct acgcatttca ccgctacaca tggagttcca ctgtcctctt ctgcactcaa  840
gtttcccagt ttccgatgcg cttcctcggt taagccgagg gctttcacat cagacttaaa  900
aaaccgcctg cgctcgcttt acgcccaata aatccggata cgcttgccac ctacgtatta  960
ccgcggctgc tggcacgtag ttagccgtgg ctttctggtt ggataccgtc acgccgacac 1020
agttactctg ccgacattct tctcaacaca gagtttacga cccgaaagct tctcactcac 1080
gcgcgtgctc catcagactg cgtcattgtg gagattccta ctgcatgctc tctccgcagt 1140
gaggatatac agttc                                                  1155

SEQ ID NO: 2              moltype = DNA   length = 23
FEATURE                   Location/Qualifiers
source                    1..23
                          mol_type = other DNA
                          organism = synthetic construct
SEQUENCE: 2
aagaacaact tccacgaaaa ggg                                           23

SEQ ID NO: 3              moltype = DNA   length = 20
FEATURE                   Location/Qualifiers
source                    1..20
                          mol_type = other DNA
                          organism = synthetic construct
SEQUENCE: 3
ggctgggtca agcatagtgt                                               20

SEQ ID NO: 4              moltype = DNA   length = 19
FEATURE                   Location/Qualifiers
source                    1..19
                          mol_type = other DNA
                          organism = synthetic construct
SEQUENCE: 4
cgcagcaact tccatgagg                                                19

SEQ ID NO: 5              moltype = DNA   length = 21
FEATURE                   Location/Qualifiers
source                    1..21
                          mol_type = other DNA
                          organism = synthetic construct
SEQUENCE: 5
agtcgcacac ctggatgtag t                                             21

SEQ ID NO: 6              moltype = DNA   length = 20
FEATURE                   Location/Qualifiers
source                    1..20
                          mol_type = other DNA
                          organism = synthetic construct
SEQUENCE: 6
tccagttgca caacttcagc                                               20

SEQ ID NO: 7              moltype = DNA   length = 20
FEATURE                   Location/Qualifiers
source                    1..20
                          mol_type = other DNA
                          organism = synthetic construct
SEQUENCE: 7
ttgtgctcag cataggcatc                                               20

SEQ ID NO: 8              moltype = DNA   length = 19
FEATURE                   Location/Qualifiers
```

-continued

```
source                   1..19
                         mol_type = other DNA
                         organism = synthetic construct
SEQUENCE: 8
ggggagatgc tccacatcc                                             19

SEQ ID NO: 9             moltype = DNA   length = 21
FEATURE                  Location/Qualifiers
source                   1..21
                         mol_type = other DNA
                         organism = synthetic construct
SEQUENCE: 9
aaaggccagg ttgatggtga g                                          21

SEQ ID NO: 10            moltype = DNA   length = 20
FEATURE                  Location/Qualifiers
source                   1..20
                         mol_type = other DNA
                         organism = synthetic construct
SEQUENCE: 10
ggcaaatcct gaagaatcca                                            20

SEQ ID NO: 11            moltype = DNA   length = 20
FEATURE                  Location/Qualifiers
source                   1..20
                         mol_type = other DNA
                         organism = synthetic construct
SEQUENCE: 11
tgctttctgt gcttgtgtcc                                            20

SEQ ID NO: 12            moltype = DNA   length = 21
FEATURE                  Location/Qualifiers
source                   1..21
                         mol_type = other DNA
                         organism = synthetic construct
SEQUENCE: 12
gcaccacaca gacgagtatg a                                          21

SEQ ID NO: 13            moltype = DNA   length = 21
FEATURE                  Location/Qualifiers
source                   1..21
                         mol_type = other DNA
                         organism = synthetic construct
SEQUENCE: 13
ggtgatgcga tcagaggatt c                                          21

SEQ ID NO: 14            moltype = DNA   length = 21
FEATURE                  Location/Qualifiers
source                   1..21
                         mol_type = other DNA
                         organism = synthetic construct
SEQUENCE: 14
agagtggacc aactgaagag t                                          21

SEQ ID NO: 15            moltype = DNA   length = 21
FEATURE                  Location/Qualifiers
source                   1..21
                         mol_type = other DNA
                         organism = synthetic construct
SEQUENCE: 15
attctctgca tttgtccgct t                                          21

SEQ ID NO: 16            moltype = DNA   length = 23
FEATURE                  Location/Qualifiers
source                   1..23
                         mol_type = other DNA
                         organism = synthetic construct
SEQUENCE: 16
atgtctgttc gatacagctc aag                                        23

SEQ ID NO: 17            moltype = DNA   length = 20
FEATURE                  Location/Qualifiers
source                   1..20
                         mol_type = other DNA
                         organism = synthetic construct
SEQUENCE: 17
ctccaccaag ggagcctttg                                            20

SEQ ID NO: 18            moltype = DNA   length = 20
```

-continued

```
FEATURE              Location/Qualifiers
source               1..20
                     mol_type = other DNA
                     organism = synthetic construct
SEQUENCE: 18
ttctgaacga gatgcgtgac                                              20

SEQ ID NO: 19        moltype = DNA  length = 20
FEATURE              Location/Qualifiers
source               1..20
                     mol_type = other DNA
                     organism = synthetic construct
SEQUENCE: 19
gcagctcaat ctccaggttc                                              20
```